United States Patent
Ogata et al.

(10) Patent No.: US 10,059,729 B2
(45) Date of Patent: Aug. 28, 2018

(54) RUTHENIUM COMPLEX, METHOD FOR PRODUCING SAME, AND USE OF SAME

(71) Applicant: Takasago International Corporation, Tokyo (JP)

(72) Inventors: Osamu Ogata, Kanagawa (JP); Hideki Nara, Kanagaw (JP); Yuji Nakayama, Kanagawa (JP)

(73) Assignee: Takasago International Corporation, Tokyo (JP)

(*) Notice: Subject to any disclaimer, the term of this patent is extended or adjusted under 35 U.S.C. 154(b) by 162 days.

(21) Appl. No.: 15/306,671

(22) PCT Filed: Apr. 24, 2015

(86) PCT No.: PCT/JP2015/062492
§ 371 (c)(1),
(2) Date: Oct. 25, 2016

(87) PCT Pub. No.: WO2015/163440
PCT Pub. Date: Oct. 29, 2015

(65) Prior Publication Data
US 2017/0044196 A1    Feb. 16, 2017

(30) Foreign Application Priority Data
Apr. 25, 2014 (JP) .................... 2014-091969

(51) Int. Cl.
| | |
|---|---|
| C07F 15/00 | (2006.01) |
| B01J 31/24 | (2006.01) |
| B01J 31/22 | (2006.01) |
| C07C 29/132 | (2006.01) |
| C07C 29/141 | (2006.01) |
| C07C 29/145 | (2006.01) |
| C07C 29/149 | (2006.01) |
| C07C 31/20 | (2006.01) |
| C07C 33/22 | (2006.01) |
| C07F 9/50 | (2006.01) |
| C07C 209/18 | (2006.01) |
| C07C 45/29 | (2006.01) |
| C07F 19/00 | (2006.01) |
| C07C 211/48 | (2006.01) |
| C07C 49/78 | (2006.01) |

(Continued)

(52) U.S. Cl.
CPC .......... *C07F 15/0046* (2013.01); *B01J 31/22* (2013.01); *B01J 31/24* (2013.01); *B01J 31/2409* (2013.01); *C07C 29/132* (2013.01); *C07C 29/141* (2013.01); *C07C 29/145* (2013.01); *C07C 29/149* (2013.01); *C07C 31/20* (2013.01); *C07C 33/22* (2013.01); *C07C 45/29* (2013.01); *C07C 49/78* (2013.01); *C07C 209/18* (2013.01); *C07C 211/48* (2013.01); *C07D 213/30* (2013.01); *C07F 9/50* (2013.01); *C07F 15/00* (2013.01); *C07F 19/00* (2013.01); *B01J 2231/643* (2013.01); *B01J 2231/70* (2013.01); *B01J 2531/0216* (2013.01); *B01J 2531/821* (2013.01); *C07B 61/00* (2013.01)

(58) Field of Classification Search
CPC ..................... C07F 15/0046; B01J 31/2409
See application file for complete search history.

(56) References Cited

U.S. PATENT DOCUMENTS

| 2011/0237814 A1 | 9/2011 | Kuriyama et al. |
| 2016/0009632 A1 | 1/2016 | Ogata et al. |

FOREIGN PATENT DOCUMENTS

| JP | 2010-527316 A | 8/2010 |
| WO | 2004096735 A2 | 11/2004 |
| WO | 2008/141439 A1 | 11/2008 |

(Continued)

OTHER PUBLICATIONS

Bianchini et al. "Anninocarbene Complexes as Intermediates in the Ruthenium-Assisted Aminolysis of Phenylacetylene to Isonitriles and Toluene" Organometallics, 1999, vol. 18, pp. 2376-2386.*

(Continued)

*Primary Examiner* — Joseph R Kosack
(74) *Attorney, Agent, or Firm* — Mintz Levin Cohn Ferris Glovsky and Popeo, P.C.; Peter F. Corless

(57) ABSTRACT

The present invention provides a novel ruthenium complex that is easy to produce and handle and that can be supplied relatively inexpensively, a method for producing this ruthenium complex, a method for producing alcohols and the like using this ruthenium complex as a catalyst, a method for producing carbonyl compounds using this ruthenium complex as a catalyst, and a method for producing N-alkylamine compounds using this ruthenium complex as a catalyst. The present invention pertains to a ruthenium complex represented by general formula (1) $RuX^1X^2(PNP)(NHC)_m(Solv)_n$ (1) (in general formula (1), $X^1$ and $X^2$ each independently represent a monovalent anionic monodentate ligand; PNP represents a tridentate aminodiphosphine ligand, NHC represents an N-heterocyclic carbene derived from a nitrogen-containing heterocyclic ring, and Solv represents a coordinating solvent; and m represents an integer from 1 to 3, n represents an integer from 0 to 2, and $1 \leq m+n \leq 3$.), a method for producing the same, a catalyst including the same, and methods for producing various organic compounds using this catalyst.

19 Claims, 1 Drawing Sheet

(51) Int. Cl.
*C07D 213/30* (2006.01)
*C07B 61/00* (2006.01)

(56) References Cited

FOREIGN PATENT DOCUMENTS

| WO | 2011/048727 A1 | 4/2011 |
| WO | 2012/039098 A1 | 3/2012 |
| WO | 2012/144650 A1 | 10/2012 |
| WO | 2014059757 A1 | 4/2014 |
| WO | 2014/136374 A1 | 9/2014 |

OTHER PUBLICATIONS

International Search Report—PCT/JP2015/062492 dated Jul. 21, 2015.
Friedrich, et al., Inorg. Chem. 2010,49, 5482-5494, pp. 5482-5494.
DeMott, et al., Chem. Sci., 2013, 4(2), 642-649.
Prechtl, et al., European Journal of Inorganic Chemistry, 2008, (22), 3493-3500.
Bianchina, et. al., Inorganica Chimica Acta, 1998, 272(1,2), 1-3.
Gregor, et al., Dalton Transactions, 2010, 39(13), 3195-3202.
Bianchina, et al., Jounral of the Chemical Society, Chemical Communications, 1994, (19), 2219-20.
European Search Report of corresponding European Application No. 15783902.8, dated Aug. 21, 2017 (6 pages).
International Preliminary Report on Patentability dated Oct. 25, 2016, International Application No. PCT/JP2015/062492 (5 pages).

\* cited by examiner

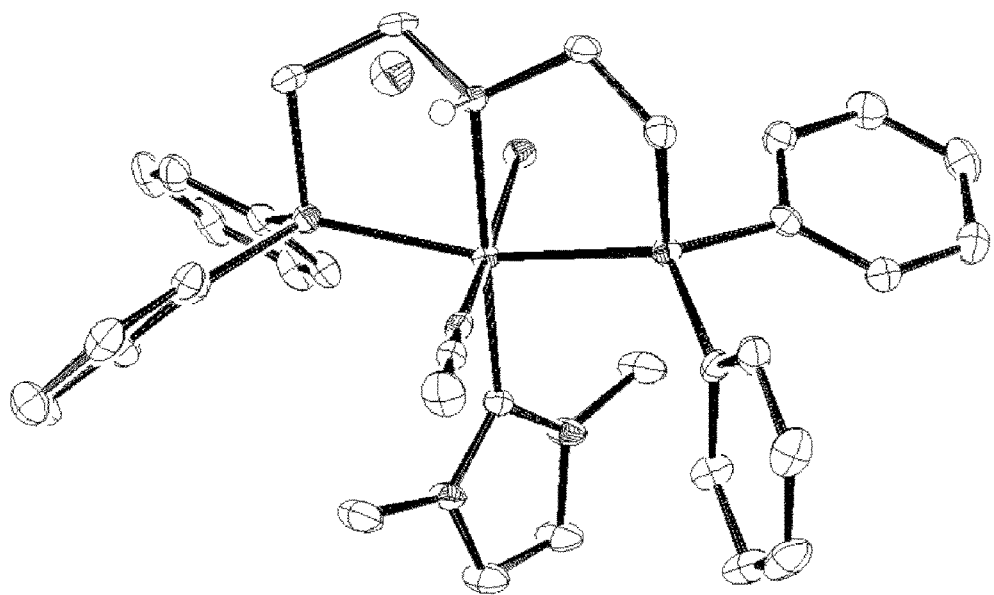

RUTHENIUM COMPLEX, METHOD FOR PRODUCING SAME, AND USE OF SAME

This application is a national Phase application filed under 35 U.S.C. § 371 of PCT International Application No. PCT/JP2015/062492, with an International Filing Date of Apr. 24, 2015, which claims under 35 U.S.C. § 119(a) the benefit of Japanese Application No. 2014-091969, filed Apr. 25, 2014, the entire contents of which are incorporated herein by reference.

TECHNICAL FIELD

The present invention relates to a ruthenium complex having a tridentate ligand and a N-heterocyclic carbene ligand, a method for producing the same, a method for producing alcohols by hydrogenation of ketones or aldehydes; a method for producing alcohols, aldehydes or hemiacetals by hydrogenation of esters; a method for producing alcohols, aldehydes, hemiaminals or amines by hydrogenation of amides; a method for producing carbonyl compounds by dehydrogenation of alcohols; and a method for producing N-alkylamine compounds via condensation between alcohols and amines using the complex as a catalyst.

BACKGROUND ART

Synthesis of alcohols, aldehydes, hemiacetals, hemiaminals and amines by reduction is industrially important reaction. In particular, hydrogenation using a transition metal catalyst is useful from the view point of reducing by-products, excellent operability, and safety of work and so on. Also optically active alcohols are important as physiologically active substances such as pharmaceuticals, agricultural chemicals and aromatics, and as synthetic intermediates thereof, and asymmetric hydrogenation of ketones, and hydrogenation of optically active aldehydes, optically active esters and optically active amides having a chiral point are useful as a method for producing optically active alcohols.

Also synthesis of carbonyl compounds by oxidation is industrially important. In particular, dehydrogenation using a transition metal catalyst is useful in terms of safety because it does not require an explosive substance such as a peroxide generally used as an oxidant.

Further, synthesis of N-alkylamine compounds is also industrially important reaction. In particular, N-alkylation reaction using a transition metal catalyst is useful as a safe procedure because it does not require a mutagen such as methyl iodide and dimethyl sulfate that are generally used as an alkylating agent.

As transition metal catalysts used in these reactions, heterogeneous catalysts using platinum or chromium as metal, and homogenous catalysts using ruthenium, iridium or rhodium as metal can be recited. Reaction using a heterogeneous catalyst generally requires high temperature and high pressure, and has a problem in terms of safety. Therefore, homogenous catalysts are industrially advantageous. In particular, a ruthenium catalyst is advantageous over an iridium catalyst or a rhodium catalyst in terms of costs.

As a catalyst used for hydrogenation of ketones, esters and so on, a ruthenium complex having a bis (phosphinoalkyl)amine as a tridentate ligand and having carbon monoxide as a monodentate ligand is reported (see Patent Document 1). Also, hydrogenation of amides, dehydrogenation of alcohols, and condensation between alcohols and amines using the ruthenium complex as a catalyst are also reported (see Patent Documents 2, 3 and 4). Although a ruthenium complex having a bis (phosphinoalkyl) amine as a tridentate ligand, and having tertiary phosphines as a monodentate ligand is reported, this ruthenium complex is not used as a catalyst (see Non Patent Document 1).

CITATION LIST

Patent Documents

Patent Document 1: WO 2011/048727 A1
Patent Document 2: WO 2012/039098 A1
Patent Document 3: WO 2012/144650 A1
Patent Document 4: WO 2014/136374 A1

Non Patent Document

Non Patent Document 1: Inorg. Chem. 2010, 49, 5482-5494

SUMMARY OF THE INVENTION

Problems to be Solved by the Invention

It is an object of the present invention to provide a ruthenium complex that can be produced inexpensively and is easy to handle, a method for producing the same, and a method for producing alcohols by hydrogenation of ketones or aldehydes; a method for producing alcohols, aldehydes or hemiacetals by hydrogenation of esters; a method for producing alcohols, aldehydes, hemiaminals or amines by hydrogenation of amides; a method for producing carbonyl compounds by oxidization of alcohols, hemiacetals or hemiaminals; and a method for producing N-alkylamine compounds via condensation between alcohols and amines using the ruthenium complex as a catalyst. In these reactions, a complex showing higher catalytic activity under a gentler reaction condition is demanded for industrial practice in terms of the cost, the problem of the residual metal, and the safety.

Means for Solving the Problems

In light of the aforementioned circumstances, the present inventors conducted intensive studies, and consequently found a ruthenium complex featured by having a bis(phosphinoalkyl)amine as a tridentate ligand and having a N-heterocyclic carbene as a monodentate ligand. The inventors found that the ruthenium complex found by the present invention can be produced inexpensively, and is easy to handle because it is powder that is weighable in air, and catalyzes hydrogenation of ketones, aldehydes, esters and amides, dehydrogenation of alcohols, hemiacetals and hemiaminals, and N-alkylation via condensation between alcohols and amines. Also, the inventors found that the ruthenium complex found by the present invention shows higher catalytic activity than a conventional ruthenium complex having carbon monoxide as a monodentate ligand, and allows gentle reaction conditions. Based on these findings, the present inventors accomplished the present invention.

The present invention pertains to the following [1] to [26].
[1] A ruthenium complex represented by the following general formula (1):

$$RuX^1X^2(PNP)(NHC)_m(Solv)_n \tag{1}$$

(in the general formula (1), $X^1$ and $X^2$ each independently represent a monovalent anionic monodentate ligand. PNP represents a tridentate ligand represented by the general formula (2):

[Chemical Formula 1]

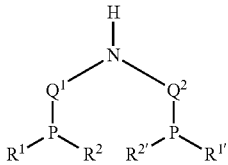

(2)

(in the general formula (2), $R^1$, $R^2$, $R^{1\prime}$ and $R^{2\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s). $R^1$ and $R^2$, and $R^{1\prime}$ and $R^{2\prime}$ each independently may bind to each other to form a ring together with the adjacent phosphorus atom. $Q^1$ and $Q^2$ each independently represent an optionally substituted alkanediyl group or an optionally substituted aralkylene group.), NHC represents an N-heterocyclic carbene derived from a nitrogen-containing heterocyclic ring, and Solv represents a coordinating solvent. m represents an integer from 1 to 3, n represents an integer from 0 to 2, and $1 \leq m+n \leq 3$.).

[2] The ruthenium complex according to [1], wherein the PNP is a tridentate ligand represented by the following general formula (3):

[Chemical Formula 2]

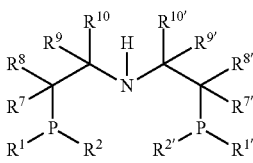

(3)

(in the general formula (3), $R^1$, $R^2$, $R^{1\prime}$ and $R^{2\prime}$ represent the groups having the same definition as in the general formula (2) $R^7$, $R^{7\prime}$, $R^8$, $R^{8\prime}$, $R^9$, $R^{9\prime}$, $R^{10}$ and $R^{10\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent (s). $R^7$, and $R^8$ or $R^9$ or $R^{10}$, $R^{7\prime}$, and $R^{8\prime}$ or $R^{9\prime}$ or $R^{10\prime}$, $R^8$, and $R^9$ or $R^{10}$, $R^{8\prime}$, and $R^{9\prime}$ or $R^{10\prime}$, $R^9$, and $R^{10}$ or $R^{9\prime}$ or $R^{10\prime}$, $R^{9\prime}$, and $R^{10}$ or $R^{10\prime}$ and $R^{10}$ and $R^{10\prime}$ each independently may bind to each other to form a ring together with the adjacent carbon atom(s).).

[3] The ruthenium complex according to [2], wherein the PNP is a tridentate ligand represented by the following general formula (4):

[Chemical Formula 3]

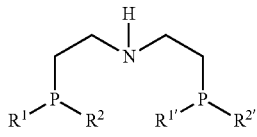

(4)

(in the general formula (4), $R^1$, $R^2$, $R^{1\prime}$ and $R^{2\prime}$ represent the groups having the same definition as in the general formula (2).).

[4] The ruthenium complex according to any one of [1] to [3], wherein $R^1$, $R^2$, $R^{1\prime}$ and $R^{2\prime}$ each independently represent an optionally substituted alkyl group, an optionally substituted aryl group or an optionally substituted aralkyl group.

[5] The ruthenium complex according to any one of [1] to [4], wherein NHC is any one of N-heterocyclic carbene selected from the group consisting of imidazole-ylidenes, dihydroimidazole-ylidenes, thiazole-ylidenes, dihydropyrimidine-ylidenes, hexahydro-1,3-diazepine-ylidenes, dihydrothiazole-ylidenes, oxazole-ylidenes, dihydrooxazole-ylidenes, tetrahydropyrimidine-ylidenes, pyrimidine-ylidenes and triazole-ylidenes.

[6] The ruthenium complex according to [5], wherein the NHC is imidazole-2-ylidenes or dihydroimidazole-2-ylidenes represented by the following general formula (5) or (6):

[Chemical Formula 4]

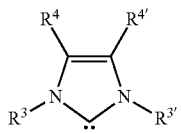

(5)

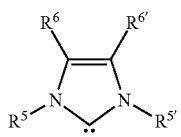

(6)

(in the general formulas (5) and (6), $R^3$, $R^{3\prime}$, $R^5$ and $R^{5\prime}$ each independently represent an alkyl group, an aryl group, an aralkyl group, an alkenyl group, an alkynyl group or a heterocyclic group, and these alkyl group, aryl group, aralkyl group, alkenyl group, alkynyl group and heterocyclic group may have substituent (s). Further, in the general formulas (5) and (6), $R^4$, $R^{4\prime}$, $R^6$ and $R^{6\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent (s). In the general formula (5), $R^3$ and $R^{3\prime}$, $R^3$ and $R^4$, $R^4$ and $R^{4\prime}$ and $R^{4\prime}$ and $R^{3\prime}$ each independently may bind to each other to form a ring together with a neighboring atom. Further, in general formula (6), $R^5$ and $R^{5\prime}$, $R^5$ and $R^6$, $R^6$ and $R^{6\prime}$ and $R^{6\prime}$ and $R^{5\prime}$ each independently may bind to each other to form a ring together with the adjacent atoms.).

[7] The ruthenium complex according to [6], wherein $R^3$, $R^{3'}$, $R^5$ and $R^{5'}$ each independently represent an optionally substituted alkyl group or an optionally substituted aryl group, and $R^4$, $R^{4'}$, $R^6$ and $R^{6'}$ each independently represent a hydrogen atom, an optionally substituted alkyl group or an optionally substituted.

[8] The ruthenium complex according to any one of [1] to [7], wherein the PNP and/or NHC is an optically active form.

[9] A method for producing the ruthenium complex according to any one of [1] to [8], wherein a ruthenium complex represented by the following general formula (7):

(in the general formula (7), $X^1$ and $X^2$ each independently represent a monovalent anionic monodentate ligand, PNP represents a tridentate ligand represented by the general formula (2), (3) or (4) or an optically active form thereof, and q represents an integer from 1 to 2) is reacted with NHC (NHC represents an N-heterocyclic carbene derived from a nitrogen-containing heterocyclic ring, or an optically active form thereof) or an NHC equivalent.

[10] A method for producing the ruthenium complex according to any one of [1] to [8], wherein a ruthenium complex represented by the following general formula (8):

(in the general formula (8), $X^1$ and $X^2$ each independently represent a monovalent anionic monodentate ligand, arene represents an aromatic compound, NHC represents an N-heterocyclic carbene derived from a nitrogen-containing heterocyclic ring or an optically active form thereof) is reacted with PNP (PNP represents a tridentate ligand represented by the general formula (2), (3) or (4) or an optically active form thereof).

[11] A method for producing alcohol by hydrogenation of ketone using the ruthenium complex according to any one of [1] to [8] as a catalyst.

[12] A method for producing alcohol by hydrogenation of aldehyde using the ruthenium complex according to any one of [1] to [8] as a catalyst.

[13] A method for producing alcohol, aldehyde or hemiacetal by hydrogenation of ester using the ruthenium complex according to any one of [1] to [8] as a catalyst.

[14] A method for producing alcohol, aldehyde, hemiaminal or amine by hydrogenation of amide using the ruthenium complex according to any one of [1] to [8] as a catalyst.

[15] A method for producing carbonyl compound by dehydrogenation of alcohol, hemiacetal or hemiaminal using the ruthenium complex according to any one of [1] to [8] as a catalyst.

[16] A method for producing N-alkylamine compound via condensation between alcohol and amine, using the ruthenium complex according to any one of [1] to [8] as a catalyst.

[17] A method for producing alcohol, aldehyde, hemiacetal, hemiaminal, amine, carbonyl compound or N-alkylamine compound according to any one of [11] to [16], wherein in place of the ruthenium complex according to any one of [1] to [8], a ruthenium complex represented by the following general formula (7)

(in the general formula (7), $X^1$ and $X^2$ each independently represent a monovalent anionic monodentate ligand, PNP represents a tridentate ligand represented by general the formula (2), (3) or (4) or an optically active form thereof, and q represents an integer from 1 to 2), and NHC (NHC represents an N-heterocyclic carbene derived from a nitrogen-containing heterocyclic ring or an optically active form thereof) or an NHC equivalent are respectively added into the reaction system to function as a catalyst.

[18] A method for producing alcohol, aldehyde, hemiacetal, hemiaminal, amine, carbonyl compound or N-alkylamine compound according to any one of [11] to [16], wherein in place of the ruthenium complex according to any one of [1] to [8], a ruthenium complex represented by the following general formula (8):

(in the general formula (8), $X^1$ and $X^2$ each independently represent a monovalent anionic monodentate ligand, arene represents an aromatic compound, NHC represents an N-heterocyclic carbene derived from a nitrogen-containing heterocyclic ring or an optically active form thereof), and PNP (PNP represents a tridentate ligand represented by the general formula (2), (3) or (4) or an optically active form thereof) are respectively added into the reaction system to function as a catalysts.

[19] A catalyst for organic reaction, including the ruthenium complex according to any one of [1] to [8].

[20] The catalyst for organic reaction according to [19], wherein the organic reaction is a reaction of reducing a functional group having an unsaturated bond by using a hydrogen donor.

[21] The catalyst for organic reaction according to [20], wherein the functional group having an unsaturated bond is a functional group selected from the group consisting of a carbonyl group, an ester group and an amide group.

[22] The catalyst for organic reaction according to [19], wherein the organic reaction is a reaction of producing carbonyl compound by dehydrogenating alcohol.

[23] The catalyst for organic reaction according to [19], wherein the organic reaction is a reaction of N-alkylating amine.

[24] The catalyst for organic reaction according to any one of [19] to [23], wherein the ruthenium complex is formed in an organic reaction system.

[25] The catalyst for organic reaction according to [24], wherein the ruthenium complex formed in an organic reaction system is formed of a ruthenium complex represented by the following general formula (7):

(in the general formula (7), $X^1$ and $X^2$ each independently represent a monovalent anionic monodentate ligand, PNP represents a tridentate ligand represented by the general formula (2), (3) or (4) or an optically active form thereof, and q represents an integer from 1 to 2), and NHC (NHC represents an N-heterocyclic carbene derived from a nitrogen-containing heterocyclic ring or an optically active form thereof) or an NHC equivalent.

[26] The catalyst for organic reaction according to [24], wherein the ruthenium complex formed in an organic reaction system is formed of a ruthenium complex represented by the following general formula (8):

(in the general formula (8), $X^1$ and $X^2$ each independently represent a monovalent anionic monodentate ligand, arene represents an aromatic compound, NHC represents an N-heterocyclic carbene derived from a nitrogen-containing heterocyclic ring, or an optically active form thereof), and PNP (PNP represents a tridentate ligand represented by the general formula (2), (3) or (4) or an optically active form thereof).

Effects of the Invention

A novel ruthenium complex of the present invention can be easily prepared from a ruthenium compound, a tridentate ligand indicated by PNP, and an N-heterocyclic carbene indicated by NHC (or an NHC equivalent), and is suited for industrial use. The novel ruthenium complex of the present invention is able to catalyze reaction in a gentle reaction condition with high catalytic activity. For example, the novel ruthenium complex of the present invention catalyzes hydrogenation of ketones, aldehydes, esters and amides in the presence of a hydrogen donor, and enables desired production of alcohols or the like. In particular, in hydrogenation of esters, production of alcohols or the like under atmospheric pressure of hydrogen that was difficult with a conventional ruthenium catalyst is enabled. Also the ruthenium complex is able to catalyze dehydrogenation of alcohols or the like, and condensation between alcohols and amines. Also, the ruthenium complex with an optically active ligand is able to catalyze asymmetric hydrogenation of ketones.

BRIEF DESCRIPTION OF DRAWINGS

FIG. 1 is an ORTEP view of X-ray structural analysis of ruthenium complex B (Example 1).

DESCRIPTION OF EMBODIMENTS

A ruthenium complex represented by the following general formula (1) of the present invention will be described.

In the general formula (1), PNP represents a tridentate ligand represented by the following general formula (2).

[Chemical Formula 5]

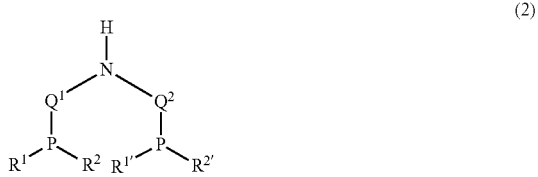

(in the general formula (2), $R^1$, $R^2$, $R^{1'}$ and $R^{2'}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s). $R^1$ and $R^2$, and $R^{1'}$ and $R^{2'}$ each independently may bind to each other to form a ring together with the adjacent phosphorus atom. $Q^1$ and $Q^2$ each independently represent an optionally substituted alkanediyl group or an optionally substituted aralkylene group.)

$R^1$, $R^2$, $R^{1'}$ and $R^{2'}$ in the general formula (2) will be described.

As an alkyl group, straight-chain, branched-chain or cyclic alkyl groups having 1 to 50 carbon atoms, preferably 1 to 20 carbon atoms, more preferably 1 to 10 carbon atoms can be recited, and concrete examples include a methyl group, an ethyl group, an n-propyl group, an isopropyl group, an n-butyl group, an isobutyl group, a s-butyl group, a tert-butyl group, an n-pentyl group, a 2-pentyl group, a 3-pentyl group, a tert-pentyl group, a 2-methylbutyl group, a 3-methylbutyl group, a 2,2-dimethylpropyl group, a 3-methylbutane-2-yl group, an n-hexyl group, an n-octyl group, a cyclopropyl group, a cyclopentyl group, a cyclohexyl group, a cyclooctyl group, a 1-bicyclo[2.2.1]heptyl group, a 2-bicyclo[2.2.1]heptyl group, a 1-bicyclo[2.2.2]octyl group, a 2-bicyclo[2.2.2]octyl group, a 1-adamantyl group (1-tricyclo[3.3.1.1]decyl group) and a 2-adamantyl group (1-tricyclo[3.3.1.1]decyl group), and more concrete examples include an isopropyl group and a cyclohexyl group.

As an aryl group, monocyclic, polycyclic or condensed cyclic aryl groups having 6 to 36 carbon atoms, preferably 6 to 18 carbon atoms, more preferably 6 to 14 carbon atoms can be recited, and concrete examples include a phenyl group, a 1-naphthyl group, a 2-naphthyl group, a 1-anthryl group, a 2-anthryl group, a 9-anthryl group, a 1-phenanthryl group, a 2-phenanthryl group, a 9-phenanthryl group, a 1-biphenyl group, a 2-biphenyl group and a 3-biphenyl group, and more concrete examples include a phenyl group.

As an aralkyl group, groups in which at least one hydrogen atom in the aforementioned alkyl group is substituted by the aforementioned aryl group can be recited, and aralkyl groups having, for example, 7 to 37 carbon atoms, preferably 7 to 20 carbon atoms, more preferably 7 to 15 carbon atoms can be recited. Concrete examples include a benzyl group, a 1-phenylethyl group, a 2-phenylethyl group and a 1-phenylpropyl group.

As an alkenyl group, straight-chain, branched-chain or cyclic alkenyl groups having, for example, 2 to 20 carbon atoms, preferably 2 to 15 carbon atoms, more preferably 2 to 10 carbon atoms can be recited, and concrete examples include a vinyl group, a 1-propenyl group, a 2-propenyl group, a 1-cyclohexenyl group and a 1-cycloheptenyl group.

As an alkynyl group, straight-chain or branched-chain alkynyl groups having, for example, 2 to 20 carbon atoms, preferably 2 to 15 carbon atoms, more preferably 2 to 10 carbon atoms can be recited, and concrete examples include an ethynyl group, a 1-propynyl group and a 2-propynyl group.

As an alkoxy group, straight-chain, branched-chain or cyclic alkoxy groups made up of an alkyl group having 1 to 20 carbon atoms, preferably 1 to 15 carbon atoms, more preferably 1 to 10 carbon atoms can be recited, and concrete examples include a methoxy group, an ethoxy group, an n-propoxy group, an isopropoxy group, an n-butoxy group, an isobutoxy group, a s-butoxy group, a tert-butoxy group, an n-pentyloxy group, a cyclopropyloxy group, a cyclopentyloxy group and a cyclohexyloxy group.

As an aryloxy group, aryloxy groups made up of a monocyclic, polycyclic or condensed cyclic aryl group having 6 to 36 carbon atoms, preferably 6 to 18 carbon atoms, more preferably 6 to 14 carbon atoms can be recited, and concrete examples include a phenoxy group, a p-methylphenoxy group and a 1-naphtyloxy group.

As an aralkyloxy group, groups in which at least one hydrogen atom in the aforementioned alkyl group of the alkoxy group is substituted by the aforementioned aryl group can be recited, and aralkyloxy groups having, for example, 7 to 20, preferably 7 to 15 carbon atoms are preferred, and concrete examples include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphtylmethoxy group and a 2-naphtylmethoxy group.

As a heterocyclic group, aliphatic heterocyclic groups and aromatic heterocyclic groups can be recited. As an aliphatic heterocyclic group, 3 to 8-membered, preferably 4 to 6-membered monocyclic aliphatic heterocyclic groups, polycyclic or condensed cyclic aliphatic heterocyclic groups having, for example, 2 to 14 carbon atoms, and containing at least one, preferably one to three heteroatoms such as a nitrogen atom, an oxygen atom and/or a sulfur atom as a heteroatom can be recited. Concrete examples of an aliphatic heterocyclic group include a 2-pyrrolidyl group, a 2-piperidinyl group, a 2-piperadinyl group, a 2-morpholinyl group, a 2-tetrahydrofuryl group, a 2-tetrahydropyranyl group and a 2-tetrahydrothienyl group.

As an aromatic heterocyclic group, 5 or 6-membered monocyclic heteroaryl groups, polycyclic or condensed cyclic heteroaryl groups having, for example, 2 to 15 carbon atoms, and containing at least one, preferably one to three heteroatoms such as a nitrogen atom, an oxygen atom and/or a sulfur atom as a heteroatom can be recited. Concrete examples include a 2-furyl group, a 3-furyl group, a 2-thienyl group, a 3-thienyl group, a 2-pyridyl group, a 3-pyridyl group, a 2-pyrimidyl group, a 2-pyrazyl group, a 2-imidazolyl group, a 4-imidazolyl group, a 2-oxazolyl group, a 2-thiazolyl group, a 2-benzfuryl group, a 3-benzfuryl group, a 2-benzthienyl group, a 3-benzthienyl group, a 2-quinolyl group, a 3-quinolyl group, a 1-isoquinolyl group, a 2-benzimidazolyl group, a 2-benzoxazolyl group and a 2-benzthiazolyl group.

An amino group may have substituent (s), and for example, an amino group in which at least one hydrogen atom in the amino group is each independently substituted by an alkyl group, an aryl group, an aralkyl group, an alkenyl group or an alkynyl group as described above can be recited, and concrete examples include an N,N-diethylamino group, an N,N-diisopropylamino group, an N,N-dicyclohexylamino group, an N,N-diphenylamino group, an N-naphtyl-N-phenylamino group and an N,N-dibenzylamino group. Also when the group has two substituents, they may bind to each other to form a ring, and concrete examples of such a group include a 1-pyrrolidinyl group and a 1-piperidinyl group. Also a 1-piperadinyl group and a 1-morpholinyl group can be recited as an amino group.

These alkyl group, aryl group, aralkyl group, alkenyl group, alkynyl group, alkoxy group, aryloxy group, aralkyloxy group and heterocyclic group may have substituent(s).

As a substituent that can be possessed by an alkyl group, an aralkyl group, an alkenyl group, an alkynyl group, an alkoxy group and an aralkyloxy group, a hydroxyl group, the aforementioned alkoxy group, the aforementioned aryloxy group, the aforementioned aralkyloxy group, the aforementioned heterocyclic group, the aforementioned amino group, a halogeno group, a silyl group, a siloxy and an acyloxy group can be recited.

As a substituent that can be possessed by an aryl group, an aryloxy group and a heterocyclic group, the aforementioned alkyl group, the aforementioned aryl group, the aforementioned aralkyl group, the aforementioned alkenyl group, the aforementioned alkynyl group, the aforementioned heterocyclic group, hydroxyl group, the aforementioned alkoxy group, the aforementioned aryloxy group, the aforementioned aralkyloxy group, the aforementioned amino group, a halogeno group, a halogenoalkyl group, a silyl group, a siloxy group and an acyloxy group can be recited.

As a halogeno group, a fluoro group, a chloro group, a bromo group and an iodo group can be recited.

As a halogenoalkyl group, groups in which at least one hydrogen atom on the aforementioned alkyl group is substituted by a halogen atom can be recited, and concrete examples include a trifluoromethyl group and an n-nonafluorobutyl group, and more concrete examples include a trifluoromethyl group.

As a silyl group, groups in which at least one hydrogen atom on a silyl group is substituted by the aforementioned alkyl group, the aforementioned aryl group, the aforementioned aralkyl group can be recited. Concrete examples include a trimethylsilyl group, a triethylsilyl group, a triisopropylsilyl group, a t-butyldimethylsilyl group, a t-butyldiphenylsilyl group and a triphenylsilyl group.

As a siloxy group, groups in which the aforementioned silyl group binds to an oxygen atom can be recited, and concrete examples include a trimethylsiloxy group, a triethylsiloxy group, a triisopropylsiloxy group, a t-butyldimethylsiloxy group, a t-butyldiphenylsiloxy group and a triphenylsiloxy group.

As an acyloxy group, acyloxy groups having 1 to 36 carbon atoms, preferably 6 to 36 carbon atoms, more preferably 6 to 18 carbon atoms, further preferably 6 to 14 carbon atoms can be recited, and concrete examples include an acetyloxy group and a benzyloxycarbonyl group.

$R^1$ and $R^2$, and $R^{1'}$ and $R^{2'}$ each independently may bind to each other to form a ring containing the adjacent phosphorus atom. Examples of a ring containing a phosphorus atom include phosphorane, phosphol, phosphinane, 2,5-dioxaphosphorane and 2,5-diazaphospholidine. These groups may have substituent(s) as described above.

$Q^1$, $Q^2$ in general formula (2) will be described.

$Q^1$ and $Q^2$ represent an optionally substituted divalent group, and preferably represent an alkanediyl group, or an optionally substituted aralkylene group.

As an alkanediyl group, straight-chain, branched-chain or cyclic alkanediyl groups having 1 to 20 carbon atoms, preferably 1 to 10 carbon atoms, more preferably 1 to 6 carbon atoms can be recited, and concrete examples include a methylene group, an ethylene group, a trimethylene group, a tetramethylene group, a pentamethylene group, a cyclopropane-1,2-diyl group, a cyclobutane-1,2-diyl group, a cyclobutane-1,3-diyl group, a cyclopentane-1,2-diyl group, a cyclopenetane-1,3-diyl group, a cyclohexane-1,2-diyl group and a cyclohexane-1,3-diyl group, and more concrete examples include an ethylene group.

As an aralkylene group, aralkylenediyl groups having 7 to 11 carbon atoms in which one hydrogen atom is removed from an aryl group in an aralkyl group such as a benzyl group or a phenethyl group can be recited, and concrete examples include a benzylene group (-Ph-CH$_2$—), a 2-phenylethylene group (-Ph-CH$_2$CH$_2$—), a 1-naphtylmethylene group (—Np—CH$_2$—) and a 2-naphtylmethylene group (—Np—CH$_2$—).

As a substituent that can be possessed by these alkanediyl group, and aralkylene group, a hydroxyl group, an alkoxy group, an aryloxy group, an aralkyloxy group, a heterocyclic group, an amino group, a halogeno group, a silyl group, a siloxy group and an acyloxy group can be recited. These groups are the same as those described above in this section.

As a further preferred PNP, a tridentate ligand represented by the following general formula (3) can be recited, and more preferably, a tridentate ligand represented by the following general formula (4) can be recited.

[Chemical Formula 6]

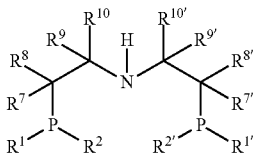

(3)

(in the general formula (3), $R^1$, $R^2$, $R^{1'}$ and $R^{2'}$ represent the groups having the same definition as in the aforementioned general formula (2). $R^7$, $R^{7'}$, $R^8$, $R^{8'}$, $R^9$, $R^{9'}$, $R^{10}$ and $R^{10'}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s). $R^7$, and $R^8$ or $R^9$ or $R^{10}$, $R^{7'}$, and $R^{8'}$ or $R^{9'}$ or $R^{10'}$, $R^8$, and $R^9$ or $R^{10}$, $R^{8'}$, and $R^{9'}$ or $R^{10'}$, $R^9$, and $R^{10}$ or $R^{9'}$ or $R^{10'}$, $R^{9'}$, and $R^{10}$ or $R^{10'}$ and $R^{10}$ and $R^{10'}$ each independently may bind to each other to form a ring together with the adjacent carbon atom(s).)

[Chemical Formula 7]

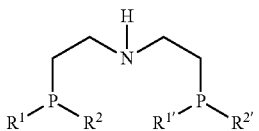

(4)

(in the general formula (4), $R^1$, $R^2$, $R^{1'}$ and $R^{2'}$ represent the groups having the same definition as in the aforementioned general formula (2).)

Description will be made for $R^7$, $R^{7'}$, $R^8$, $R^{8'}$, $R^9$, $R^{9'}$, $R^{10}$ and $R^{10'}$ in general formula (3). As an alkyl group, an aryl group, an aralkyl group, an alkenyl group, an alkynyl group, an alkoxy group, an aryloxy group, an aralkyloxy group, a heterocyclic group and an amino group, the same groups as specifically described in the description of $R^1$, $R^2$, $R^{1'}$ and $R^{2'}$ in the aforementioned general formula (2) can be recited.

These alkyl group, aryl group, aralkyl group, alkenyl group, alkynyl group, alkoxy group, aryloxy group, aralkyloxy group and heterocyclic group may have substituent(s).

As a substituent that can be possessed by an alkyl group, an aralkyl group, an alkenyl group, an alkynyl group, an alkoxy group and an aralkyloxy group, a hydroxyl group, an alkoxy group, an aryloxy group, an aralkyloxy group, a heterocyclic group, an amino group, a halogeno group, a silyl group, a siloxy group and an acyloxy group can be recited. Among these groups, as an alkoxy group, an aryloxy group, an aralkyloxy group, a heterocyclic group, an amino group, a halogeno group, a silyl group, a siloxy group and an acyloxy group, the same groups as specifically described in the description of $R^1$, $R^2$, $R^{1'}$ and $R^{2'}$ in the aforementioned general formula (2) can be recited.

As a substituent that can be possessed by an aryl group, an aryloxy group and a heterocyclic group, an alkyl group, an aryl group, an aralkyl group, an alkenyl group, an alkynyl group, a hydroxyl group, an alkoxy group, an aryloxy group, an aralkyloxy group, a heterocyclic group, an amino group, a halogeno group, a silyl group, a siloxy group and an acyloxy group can be recited. Among these groups, as an alkyl group, an aryl group, an aralkyl group, an alkenyl group, an alkynyl group, an alkoxy group, an aryloxy group, an aralkyloxy group, a heterocyclic group, an amino group, a halogeno group, a silyl group, a siloxy group and an acyloxy group, the same groups as specifically described in the description of $R^1$, $R^2$, $R^{1'}$ and $R^{2'}$ in the aforementioned general formula (2) can be recited.

NHC in general formula (1) will be described.

NHC represents an N-heterocyclic carbene derived from a nitrogen-containing heterocyclic ring. As a nitrogen-containing heterocyclic ring, 3 to 8-membered, preferably 4 to 6-membered monocyclic, polycyclic, or condensed cyclic nitrogen-containing heterocyclic rings having at least one, preferably one to three nitrogen atoms as a heteroatom, and optionally containing one to three heteroatoms such as oxygen atoms and/or sulfur atoms can be recited. Carbene indicates the state having a divalent carbon atom with no electric charge, and the nitrogen-containing heterocyclic ring in which a carbon atom is in the state capable of coordinating on a ruthenium atom in a carbene state or in a divalent carbon atom is referred to as "N-heterocyclic carbene". Examples of a preferred N-heterocyclic carbene include imidazole-ylidenes derived from imidazole, dihydroimidazole-ylidenes ylidenes derived from dihydroimidazole, dihydropyrimidine-ylidenes derived from dihydropyrimidine, hexahydro-1,3-diazepine-ylidenes derived from tetrahydro-1,3-diazepine, thiazole-ylidenes derived from thiazole, dihydrothiazole-ylidenes derived from dihydrothiazole, oxazole-ylidenes derived from oxazole, dihydrooxazole-ylidenes derived from dihydrooxazole, tetrahydropyrimidine-ylidenes derived from tetrahydropyrimidine, pyrimidine-ylidenes derived from pyrimidine and triazole-ylidenes derived from triazole. In preferred NHC, imidazole-2-ylidenes represented by the following general formula (5), and dihydroimidazole-2-ylidenes represented by the general formula (6) can be recited.

[Chemical Formula 8]

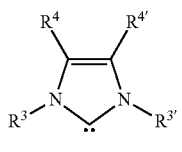

(5)

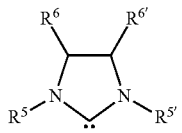

(6)

(in the general formulas (5) and (6), $R^3$, $R^{3'}$, $R^5$ and $R^{5'}$ each independently represent an alkyl group, an aryl group, anaralkyl group, an alkenyl group, an alkynyl group or a heterocyclic group, and these alkyl group, aryl group, aralkyl group, alkenyl group, alkynyl group and heterocyclic group may have substituent (s). In the general formulas (5) and (6), $R^4$, $R^{4'}$, $R^6$ and $R^{6'}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s). In general formula (5), $R^3$ and $R^{3'}$, $R^3$ and $R^4$, $R^4$ and $R^{4'}$ and $R^{4'}$ and $R^{3'}$ each independently may bind to each other to form a ring together with the adjacent atoms. In general formula (6), $R^5$ and $R^{5'}$, $R^5$ and $R^6$, $R^6$ and $R^{6'}$ and $R^{6'}$ and $R^{5'}$ each independently may bind to each other to form a ring together with the adjacent atoms.)

$R^3$, $R^{3'}$, $R^5$ and $R^{5'}$ in the general formulas (5) and (6) will be described.

As an alkyl group, an aryl group, an aralkyl group, an alkenyl group, an alkynyl group and a heterocyclic group, the same groups as specifically described in the description of $R^1$, $R^2$, $R^{1'}$ and $R^{2'}$ in the aforementioned general formula (2) can be recited. These groups may have substituent(s).

As a substituent that can be possessed when $R^3$, $R^{3'}$, $R^5$ and $R^{5'}$ each independently represent an alkyl group, an aralkyl group, an alkenyl group or an alkynyl group, an alkoxy group, an aryloxy group, an aralkyloxy group, a hydroxyl group, a heterocyclic group, an amino group, a halogeno group, a silyl group and an acyloxy group can be recited. Among these groups, as an alkoxy group, an aryloxy group, an aralkyloxy group, a heterocyclic group, an amino group, a halogeno group, a silyl group and an acyloxy group, the same groups as specifically described in the description of $R^1$, $R^2$, $R^{1'}$ and $R^{2'}$ in the aforementioned general formula (2) can be recited.

As a substituent that can be possessed when $R^3$, $R^{3'}$, $R^5$ and $R^{5'}$ each independently represent an aryl group or a heterocyclic group, an alkyl group, an aryl group, an aralkyl group, an alkenyl group, an alkynyl group, an alkoxy group, an aryloxy group, an aralkyloxy group, a heterocyclic group, hydroxyl group, an amino group, a halogeno group, an alkyl halogeno group, a silyl group and an acyloxy group can be recited. Among these groups, as an alkyl group, an aryl group, an aralkyl group, an alkenyl group, an alkynyl group, an alkoxy group, an aryloxy group, an aralkyloxy group, a heterocyclic group, an amino group, a halogeno group, an alkyl halogeno group, a silyl group and an acyloxy group, the same groups as specifically described in the description of $R^1$, $R^2$, $R^{1'}$ and $R^{2'}$ in the aforementioned general formula (2) can be recited.

$R^4$, $R^{4'}$, $R^6$ and $R^{6'}$ in the general formulas (5) and (6) will be described.

As an alkyl group, an aryl group, an aralkyl group, an alkenyl group, an alkynyl group, an alkoxy group, an aryloxy group, an aralkyloxy group, a heterocyclic group and an amino group, the same groups as specifically described in the description of $R^1$, $R^2$, $R^{1'}$ and $R^{2'}$ in the aforementioned general formula (2) can be recited. Among these groups, an alkyl group, an aryl group, an aralkyl group, an alkenyl group, an alkynyl group, an alkoxy group, an aryloxy group, an aralkyloxy group and a heterocyclic group may have substituent(s).

As a substituent that can be possessed when $R^4$, $R^{4'}$, $R^6$ and $R^{6'}$ each independently represent an alkyl group, an aralkyl group, an alkenyl group, an alkynyl group, an alkoxy group or an aralkyloxy group, a hydroxyl group, an alkoxy group, an aryloxy group, an aralkyloxy group, a heterocyclic group, an amino group, a halogeno group, a silyl group and an acyloxy group can be recited. Among these groups, as an alkoxy group, an aryloxy group, an aralkyloxy group, a heterocyclic group, an amino group, a halogeno group, a silyl group and an acyloxy group, the same groups as specifically described in the description of $R^1$, $R^2$, $R^{1'}$ and $R^{2'}$ in the aforementioned general formula (2) can be recited.

As a substituent that can be possessed when $R^4$, $R^{4'}$, $R^6$ and $R^{6'}$ each independently represent an aryl group, an aryloxy group or a heterocyclic group, an alkyl group, an aryl group, an aralkyl group, an alkenyl group, an alkynyl group, hydroxyl group, an alkoxy group, an aryloxy group, an aralkyloxy group, a heterocyclic group, an amino group, a halogeno group, an alkyl halogeno group, a silyl group and an acyloxy group can be recited. Among these groups, as an alkyl group, an aryl group, an aralkyl group, an alkenyl group, an alkynyl group, an alkoxy group, an aryloxy group, an aralkyloxy group, a heterocyclic group, an amino group, a halogeno group, an alkyl halogeno group, a silyl group and an acyloxy group, the same groups as specifically described in the description of $R^1$, $R^2$, $R^{1'}$ and $R^{2'}$ in the aforementioned general formula (2) can be recited.

Concrete examples of imidazole-2-ylidenes represented by general formula (5) include those indicated by the structural formulas: 1,3-dimethylimidazole-2-ylidene,
1,3-diisopropylimidazole-2-ylidene,
1,3-di-tert-butylimidazole-2-ylidene,
1,3-dicyclohexylimidazole-2-ylidene,
1,3-bis(2,4,6-trimethylphenyl)imidazole-2-ylidene,
1,3-dimethylbenzimidazole-2-ylidene,
1,3-diisopropylbenzimidazole-2-ylidene,
1,3-di-tert-butylbenzimidazole-2-ylidene,
1,3-dicyclohexylbenzimidazole-2-ylidene,
1,3-bis(2,4,6-trimethylphenyl)benzimidazole-2-ylidene,
1,3,4,5-tetramethylimidazole-2-ylidene,
1,3-diisopropyl-4,5-dimethylimidazole-2-ylidene,
1,3-di-tert-butyl-4,5-dimethylimidazole-2-ylidene,
1,3-dicyclohexyl-4,5-dimethylimidazole-2-ylidene and
1,3-bis(2,4,6-trimethylphenyl)-4,5-dimethylimidazole-2-ylidene.

Concrete examples of dihydroimidazole-2-ylidenes represented by the general formula (6) include those indicated by the structural formulas:
1,3-dimethyldihydroimidazole-2-ylidene, 1,3-diisopropyl dihydroimidazole-2-ylidene,
1,3-di-tert-butyldihydroimidazole-2-ylidene,
1,3-dicyclohexyldihydroimidazole-2-ylidene and
1,3-bis(2,4,6-trimethylphenyl)dihydroimidazole-2-ylidene.

[Chemical Formula 9]

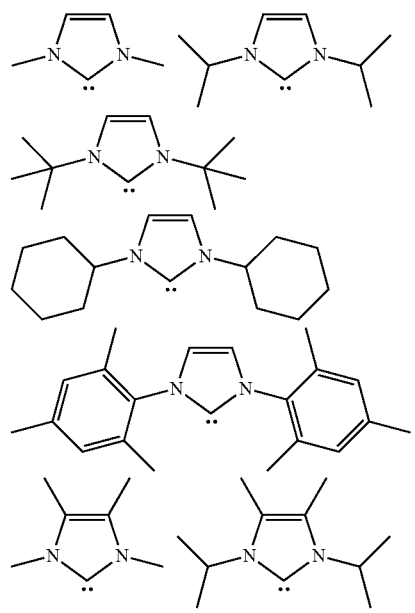

-continued

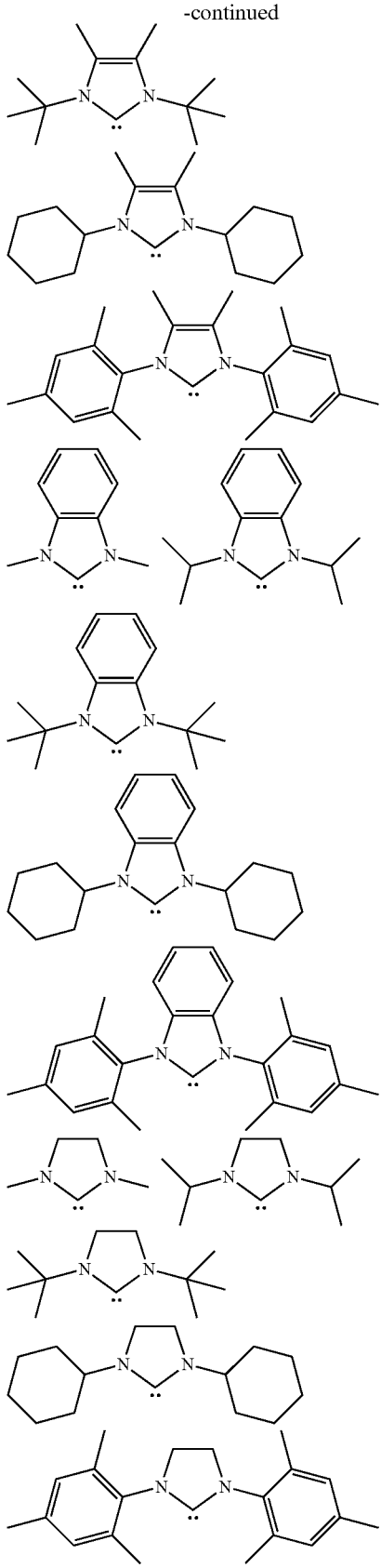

X¹ and X² in the general formula (1) each independently represent a monovalent anionic monodentate ligand. A monovalent anionic monodentate ligand represents a functional group having a monovalent negative charge and capable of single-bonding with metal in a metal complex, a negative ion capable of functioning as a counter ion for a metal complex, or a group concurrently having both of these properties, and concrete examples (name of functional group/ion, the general formula is represented in parentheses) include a hydride/hydride ion (—H/H⁻), a hydroxyl group/hydroxide ion (—OH/HO⁻), an alkoxy group/alkoxide ion (—OR/RO⁻), an aryloxy group/aryloxide ion (—OAr/ArO⁻), an aralkyloxy group/aralkyloxide ion (—OAral/AralO⁻), an acyloxy group/carboxylate ion (—OC(=O)R/RCO₂⁻), a sulfonyloxy group/sulfonate ion (—OSO₂R/RSO₃⁻), a halogeno group/halide ion (—X/X⁻), a hydrogencarbonate ion (HCO₃⁻), a tetrahydroborate ion (BH₄⁻), a tetrafluoroborate ion (BF₄⁻), a tetraarylborate ion (BAr₄⁻), a perchlorate ion (ClO₄⁻), a hexafluorophosphorate ion (PF₆⁻), a hexafluoroantimonate ion (SbF₆⁻), a tetrahydroaluminate ion (AlH₄⁻), a tetrahydroxoaluminate ion ([Al(OH)₄]⁻), a bis (2-methoxyethoxy) dihydroaluminate ion (AlH₂ (OCH₂CH₂OCH₃)₂⁻), a trihydrocyanoborate ion (BH₃CN), a triethylhydroborate ion (BH(Et)₃⁻) and a tris (2-butyl)hydroborate ion (BH(sec-Bu)₃⁻), and preferred examples include a hydride/hydride ion (—H/H⁻), a halogeno group/halide ion (—X/X⁻) and a tetrahydroborate ion (BH₄⁻).

As an alkoxy group/alkoxide ion, for example, an alkoxy group/alkoxide ion having 1 to 10 carbon atoms, preferably an alkoxy group/alkoxide ion having 1 to 4 carbon atoms can be recited, and concrete examples include a methoxy group/methoxide ion, an ethoxy group/ethoxide ion, a 1-propoxy group/1-propoxide ion, a 2-propoxy group/2-propoxide ion, a 1-butoxy group/1-butoxide ion, a 2-butoxy group/2-butoxide ion and a tert-butoxy group/tert-butoxide ion.

As an aryloxy group/aryloxide ion, for example, an aryloxy group/aryloxide ion having 6 to 14 carbon atoms, preferably an aryloxy group/aryloxide ion having 6 to 10 carbon atoms can be recited, and concrete examples include a phenoxy group/phenoxide ion, a p-methylphenoxy group/p-methylphenoxide ion, a 2,4,6-trimethylphenoxy group/2,4,6-trimethylphenoxide ion, a p-nitrophenoxy group/p-nitrophenoxide ion, a pentafluorophenoxy group/pentafluorophenoxide ion, a 1-naphtyloxy group/1-naphtyloxide ion and a 2-naphtyloxy group/2-naphtyloxide ion.

As an aralkyloxy group/aralkyloxide ion, for example, an aralkyloxy group/aralkyloxide ion having 7 to 20 carbon atoms, preferably an aralkyloxy group/aralkyloxide ion having 7 to 15 carbon atoms can be recited, and concrete examples include a benzyloxy group/benzyloxide ion, a 1-phenylethoxy group/1-phenylethoxide ion and a 2-phenylethoxy group/2-phenylethoxide ion.

As an acyloxy group/carboxylate ion, a carboxyl group/carboxylate ion having, for example, 1 to 18 carbon atoms, preferably 1 to 6 carbon atoms can be recited, and concrete examples include a formyloxy group/formate ion, an acetoxy group/acetate ion, a trifluoroacetoxy group/trifluoroacetate ion, a propanoyloxy group/propionate ion, an acryloyloxy group/acrylate ion, a butanoyloxy group/butyrate ion, a pivaloyloxy group/pivalate ion, a pentanoyloxy group/valerate ion, a hexanoyloxy group/caproate ion, a benzyloxy group/benzoate ion and a pentafluorobenzoyloxy group/pentafluorobenzoate ion.

Concrete examples of a sulfonyloxy group/sulfonate ion include a methanesulfonyloxy group/methanesulfonate ion, a trifluoromethanesulfonyloxy group/trifluoromethanesulfonate ion, an n-nonafluorobutanesulfonyloxy group/n-nonafluorobutanesulfonate ion, a p-toluenesulfonyloxy group/p-toluenesulfonate ion and a 10-camphor-sulfonyloxy group/10-camphor-sulfonate ion.

Concrete examples of a halogeno group/halide ion include a fluoro group/fluoride ion, a chloro group/chloride ion, a bromo group/bromide ion and an iodo group/iodide ion, and preferred concrete examples include a chloro group/chloride ion and an iodo group/iodide ion.

Concrete examples of a tetraarylborate ion include a tetraphenylborate ion, a tetrakis (pentafluorophenyl) borate ion and a tetrakis[3,5-bis(trifluoromethyl)phenyl]borate ion.

Non-limiting examples of a ruthenium compound for producing a ruthenium complex in the present invention include inorganic ruthenium compounds such as ruthenium trichloride hydrate, ruthenium tribromide hydrate and ruthenium triiodide hydrate, tetra(dimethylsulfoxide)dichlororuthenium (RuCl$_2$(DMSO)$_4$), dichloro(1,5-cyclooctadiene)ruthenium (II) polymer ([Ru(cod)Cl$_2$]$_n$), dichloro(norbornadiene)ruthenium (II) polymer ([Ru(nbd)Cl$_2$]$_n$), bis (2-methallyl) (1,5-cyclooctadiene)ruthenium (II) ((cod)Ru (2-methallyl)$_2$), dichloro(benzene)ruthenium (II) dimer ([Ru(benzene)Cl$_2$]$_2$), dibromo (benzene) ruthenium (II) dimer ([Ru (benzene)Br$_2$]$_2$), diiodo (benzene) ruthenium (II) dimer ([Ru (benzene) I$_2$]$_2$), dichloro(p-cymene)ruthenium (II) dimer ([Ru(p-cymene)Cl$_2$]2), dibromo(p-cymene)ruthenium (II) dimer ([Ru(p-cymene)Br$_2$]$_2$), diiodo(p-cymene) ruthenium (II) dimer ([Ru(p-cymene)I$_2$]$_2$), dichloro(mesitylene)ruthenium (II) dimer ([Ru(mesitylene)Cl$_2$]$_2$), dibromo (mesitylene)ruthenium (II) dimer ([Ru(mesitylene)Br$_2$]$_2$), diiodo(mesitylene)ruthenium (II) dimer ([Ru(mesitylene) I$_2$]$_2$), dichloro(hexamethylbenzene)ruthenium (II) dimer ([Ru (hexamethylbenzene) Cl$_2$]$_2$), dibromo(hexamethylbenzene)ruthenium (II) dimer ([Ru (hexamethylbenzene) Br$_2$]$_2$), diiodo(hexamethylbenzene)ruthenium (II) dimer ([Ru (hexamethylbenzene) I$_2$]$_2$), dichlorotris (triphenyl) phosphine (RuCl$_2$(PPh$_3$)$_3$), dibromotris (triphenyl)phosphine (RuBr$_2$ (PPh$_3$)$_3$), diiodotris (triphenyl)phosphine (RuI$_2$ (PPh$_3$)$_3$), tetrahydrotris(triphenylphosphine)ruthenium (IV) (RuH$_4$ (PPh$_3$)$_3$), hydrochlorotris(triphenylphosphine)ruthenium (II) (RuClH(PPh$_3$)$_3$), acetatetris (triphenylphosphine)ruthenium (II) (RuH(OAc) (PPh$_3$)$_3$) and dihydrotetrakis(triphenylphosphine)ruthenium (II) (RuH$_2$ (PPh$_3$)$_4$).

A ruthenium complex represented by general formula (1) of the present invention can be easily produced from PNP, a ruthenium compound and NHC or an NHC equivalent.

As an NHC equivalent, those converted into N-heterocyclic carbene in a system can be recited. Preferred examples include an N-heterocyclic carbene silver complex, an azolium salt and an azolium carboxylate zwitterion, and concrete examples include an N-heterocyclic carbene silver complex, an azolium salt and an azolium carboxylate zwitter ion represented by the following structural formula that is converted in the system into imidazole-2-ylidenes, dihydroimidazole-2-ylidenes. As X in the following drawing, a halogeno group/halide ion such as a fluoro group/fluoride ion, a chloro group/chloride ion, a bromo group/bromide ion and an iodo group/iodide ion, and an anion such as a perchlorate ion (CO$_4^-$), atetrafluoroborate ion (BF$_4^-$), a hexafluorophosphorate ion (PF$_6^-$) and a hexafluoroantimonate ion (SbF$_6^-$) can be recited.

[Chemical Formula 10]

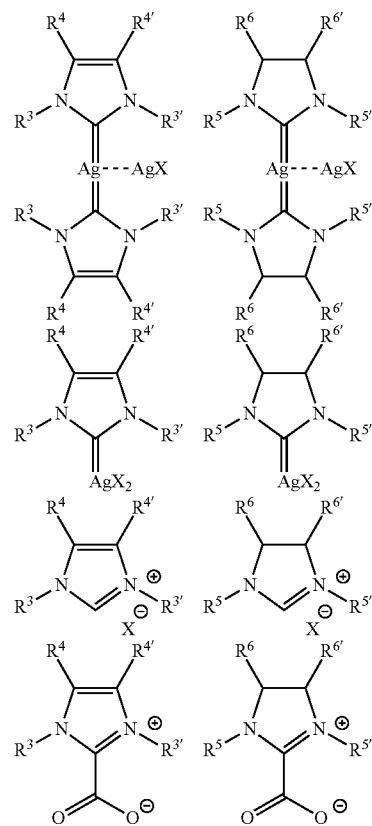

m and n in the general formula (1) will be described. m represents an integer from 1 to 3, n represents an integer from 0 to 2, and 1≤m+n≤3.

Concretely, when m=1, and n=0, a ruthenium complex represented by the general formula (1) is RuX$^1$X$^2$ (PNP) (NHC), when m=1, and n=1, a ruthenium complex represented by the general formula (1) is [RuX$^1$(PNP) (NHC) (Solv)]X$^2$, when m=1, and n=2, a ruthenium complex represented by the general formula (1) is [Ru (PNP) (NHC) (Solv)$_2$]X$^1$X$^2$, when m=2, and n=0, a ruthenium complex represented by the general formula (1) is [RuX$^1$(PNP) (NHC)$_2$]X$^2$, when m=2, and n=1, a ruthenium complex represented by the general formula (1) is [Ru(PNP) (NHC)$_2$ (Solv)]X$^1$X$^2$, when m=3, and n=0, a ruthenium complex represented by the general formula (1) is [Ru (PNP) (NHC)$_3$]X$^1$X$^2$. More preferred concrete examples include those when m=1, and n=0 and when m=1, and n=1.

Solv in the general formula (1) will be described. Solv represents a coordinating solvent, and examples include aromatic hydrocarbons such as toluene and xylene, ethers such as diethyl ether, tetrahydrofuran, methyl tert-butyl ether and cyclopentyl methyl ether, alcohols such as methanol, ethanol, isopropyl alcohol, n-butyl alcohol, 2-butanol and tert-butyl alcohol, polyalcohols such as ethylene glycol, propylene glycol, 1,2-propane diol and glycerin, amides such as dimethylformamide, dimethylacetamide, nitriles such as acetonitrile, sulfoxides such as dimethylsulfoxide and water, and preferred examples include aromatic hydrocarbons, ethers, alcohols, polyalcohols, amides, nitriles and sulfoxides. Preferred concrete examples include tetrahydrofuran, methanol, ethanol, isopropyl alcohol, dimethylformamide, acetonitrile and dimethylsulfoxide, and more preferred concrete examples include acetonitrile.

Such a coordinating solvent may be introduced by solvation of a solvent used in reaction during the producing process of a ruthenium complex represented by the general formula (1). Also, such a coordinating solvent may be introduced by adding a coordinating solvent in a ruthenium complex that is not solvated in the general formula (1) (ruthenium complex in which n=0 in the general formula (1)).

Also, Solv in the general formula (1) may be replaced by addition of other coordinating solvent.

While the ruthenium complex of the present invention produced in this manner can have stereoisomers depending on the coordination mode of the ligand and conformation, the complex used in the reaction may be a mixture of these stereoisomers or may be a pure isomer.

Non-limiting examples of the method for producing a ruthenium complex represented by the general formula (1) include:

a method for producing a ruthenium complex featured by reacting a ruthenium complex represented by the following general formula (7):

[RuX$^1$X$^2$(PNP)]$_q$     (7)

(in the general formula (7), X$^1$ and X$^2$ each independently represent a monovalent anionic monodentate ligand, PNP represents a tridentate ligand represented by the general formula (2), (3) or (4) or an optically active form thereof, and q represents an integer from 1 to 2.), with NHC (NHC represents an N-heterocyclic carbene derived from a nitrogen-containing heterocyclic ring or an optically active substance thereof.) or an NHC equivalent, and a method for producing a ruthenium complex featured by reacting a ruthenium complex represented by the following general formula (8):

RuX$^1$X$^2$(arene)(NHC)     (8)

(in the general formula (8), X$^1$ and X$^2$ each independently represent a monovalent anionic monodentate ligand, arene represents an aromatic compound, NHC represents an N-heterocyclic carbene derived from a nitrogen-containing heterocyclic ring, or an optically active form thereof.) with PNP (PNP represents a tridentate ligand represented by the general formula (2), (3) or (4) or an optically active form thereof.).

X$^1$ and X$^2$ in the general formulas (7) and (8) represent the same monovalent anionic monodentate ligand as the monovalent anionic monodentate ligand specifically described in the aforementioned general formula (1).

In the general formula (8), arene represents an aromatic compound, and concrete examples include p-cymene, benzene, toluene, o-xylene, m-xylene, p-xylene, mesitylene, hexamethylbenzene, ethylbenzene, cumene, t-butylbenzene, styrene, allylbenzene, phenylacetylene, benzyl alcohol, phenethyl alcohol, anisole, ethoxybenzene, methyl benzoate, ethyl benzoate, indan, tetralin and 2-indanol, and preferred examples include p-cymene and benzene.

In the production of a ruthenium complex represented by the general formula (1), it is preferred to use solvent(s). Examples of the solvent that can be used include aliphatic hydrocarbons such as hexane and heptane, aromatic hydrocarbons such as toluene and xylene, halogenated hydrocarbons such as methylene chloride and chlorobenzene, ethers such as diethyl ether, tetrahydrofuran, methyl tert-butyl ether and cyclopentyl methyl ether, alcohols such as methanol, ethanol, isopropyl alcohol, n-butyl alcohol, 2-butanol and tert-butyl alcohol, polyalcohols such as ethylene glycol, propylene glycol, 1,2-propane diol and glycerin, amides such as dimethylformamide, and dimethylacetamide and nitriles such as acetonitrile, sulfoxides such as dimethylsulfoxide and water, and preferred examples include aliphatic hydrocarbons, aromatic hydrocarbons, ethers, alcohols, polyalcohols, amides, nitriles and sulfoxides. Preferred concrete examples include tetrahydrofuran, methanol, ethanol, isopropyl alcohol, dimethylformamide, acetonitrile and dimethylsulfoxide, and more preferred concrete examples include methanol, ethanol and acetonitrile. These solvents may be used solely or in combination of two or more kinds.

While the use amount of the solvent is not particularly limited as long as the reaction proceeds, it is appropriately selected in the range of normally 0.001 mol/L (substance amount of Ru/solvent amount) to 20 mol/L, preferably 0.005 mol/L to 10 mol/L, more preferably 0.01 mol/L to 5 mol/L. The reaction is conducted under stirring as needed.

In the present reaction, additive(s) may be added appropriately. Examples of an additive include a Brøsted acid, a salt of Brøstedacid, and a basic compound. Concrete examples of a Brønsted acid include hydrofluoric acid, hydrochloric acid, hydrobromic acid, hydroiodic acid, acetic acid, benzoic acid, trifluoromethanesulfonic acid, tetrafluoroboric acid and hexafluorophosphoric acid. As a salt of Brønsted acid, for example, metal salts formed of Brønsted acid can be recited, preferably metal halides and the like can be recited, and preferred concrete examples include lithium chloride, lithium bromide, lithiumiodide, sodium fluoride, sodium bromide, sodium iodide, potassium fluoride and potassium bromide. Examples of a basic compound include metal hydroxides such as lithium hydroxide, sodium hydroxide, potassium hydroxide and cesium hydroxide, metal hydrides such as lithium hydride, sodium hydride, potassium hydride, lithium borohydride, sodium borohydride, potassium borohydride, aluminum lithium hydride and diisobutylaluminum hydride, and metal alkoxides such as lithium methoxide, lithium isopropoxide, lithium tert-butoxide, sodium methoxide, sodium ethoxide, sodium isopropoxide, sodium tert-butoxide, potassium methoxide, potassium ethoxide, potassium isopropoxide and potassium tert-butoxide, and preferred concrete examples include sodium borohydride, sodium methoxide and potassium tert-butoxide. Also, NHC and an equivalent thereof may be added as an additive.

The present reaction is desirably conducted in an inert gas atmosphere, a hydrogen gas atmosphere or an air atmosphere. As an inert gas, concretely, argon gas, nitrogen gas and the like can be recited. These gases and atmospheric air may be used individually or used as a mixed gas. The reaction temperature is appropriately selected normally in the range of −50° C. to 200° C., preferably in the range of −20° C. to 150° C., more preferably in the range of 0° C. to 100° C. While the reaction time naturally varies depending on the base, the solvent, the reaction temperature and other conditions, it is appropriately selected normally in the range of 1 minute to 72 hours, preferably in the range of 1 minute to 24 hours, more preferably in the range of 5 minutes to 12 hours.

The ruthenium complex produced by the present reaction may be subject to a post treatment, isolation and purification as needed. As a method of a post treatment, for example, concentration, solvent replacement, washing, extraction, backward extraction, filtration and crystallization by addition of a poor solvent can be recited, and these may be conducted solely or in combination. As a method for isolation and purification, for example, drying up of a reaction solution, column chromatography, recrystallization and washing of crystals with a poor solvent can be recited, and these may be conducted solely or in combination.

A ruthenium complex represented by the general formula (1) of the present invention is useful as a catalyst in hydrogenation of ketones, aldehydes, esters and amides. Also, a ruthenium complex represented by the general formula (1) of the present invention is useful as a catalyst in dehydrogenation of alcohols, hemiacetals and hemiaminals, and N-alkylation via condensation between alcohols and amines.

Therefore, the present invention provides a catalyst for an organic reaction, containing a ruthenium complex represented by the general formula (1).

A method for producing alcohols by hydrogenation of ketones will be described.

The method for producing alcohols by hydrogenation of ketones in the present invention is a method for producing alcohols from ketones by using a ruthenium complex represented by the general formula (1) and a hydrogen donor, and a method represented by the following scheme (9) can be recited:

[Chemical Formula 11]

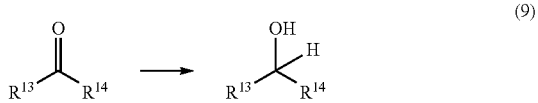

(9)

(in the scheme (9), $R^{13}$ and $R^{14}$ each independently represent an alkyl group, an aryl group, an aralkyl group, an alkenyl group, an alkynyl group, a heterocyclic group or a carbonyl group having one monovalent group, and preferably represent an alkyl group or an aryl group. Also, $R^{13}$ and $R^{14}$ may bind to each other to form a ring together with the adjacent atom. Also, these alkyl group, aryl group, aralkyl group, alkenyl group, alkynyl group and heterocyclic group may have substituent(s).)

As an alkyl group, straight-chain, branched-chain or cyclic alkyl groups having 1 to 50 carbon atoms, preferably 1 to 30 carbon atoms, more preferably 1 to 20 carbon atoms can be recited, and concrete examples include a methyl group, an ethyl group, an n-propyl group, an isopropyl group, an n-butyl group, an isobutyl group, a s-butyl group, a tert-butyl group, an n-pentyl group, a 2-pentyl group, a 3-pentyl group, a tert-pentyl group, a 2-methylbutyl group, a 3-methylbutyl group, a 2,2-dimethylpropyl group, a 3-methylbutane-2-yl group, an n-hexyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, a cyclopropyl group, a cyclopentyl group, a cyclohexyl group, a cyclooctyl group, a 1-bicyclo[2.2.1]heptyl group, a 2-bicyclo[2.2.1]heptyl group, a 1-bicyclo[2.2.2]octyl group, a 2-bicyclo[2.2.2]octyl group, a 1-adamantyl group (1-tricyclo[3.3.1.1]decyl group) and a 2-adamantyl group (1-tricyclo[3.3.1.1]decyl group), more concrete examples include a methyl group, an ethyl group, an isopropyl group and a cyclohexyl group, and further concrete examples include a methyl group.

As an aryl group, monocyclic, polycyclic or condensed cyclic aryl groups having 6 to 36 carbon atoms, preferably 6 to 18 carbon atoms, more preferably 6 to 14 atoms can be recited, and concrete examples include a phenyl group, a 1-naphthyl group, a 2-naphthyl group, a 1-anthryl group, a 2-anthryl group, a 9-anthryl group, a 1-phenanthryl group, a 2-phenanthryl group, a 9-phenanthryl group, a 1-biphenyl group, a 2-biphenyl group and a 3-biphenyl group, and more concrete examples include a phenyl group.

As an aralkyl group, groups in which at least one hydrogen atom in the aforementioned alkyl group is substituted by the aforementioned aryl group can be recited, and aralkyl groups having, for example, 7 to 50 carbon atoms, preferably 7 to 30 carbon atoms, more preferably 7 to 20 carbon atoms can be recited. Concrete examples include a benzyl group, a 1-phenylethyl group, a 2-phenylethyl group, a 1-phenylpropyl group, a 1-phenylbutyl group, a 1-phenylpentyl group, a 1-phenylhexyl group, a 1-phenylheptyl group, a 1-phenyloctyl group, a 1-phenylnonyl group, a 1-phenyldecyl group, a 1-phenylundecyl group, a 1-phenyldodecyl group, a 1-phenyltridecyl group and a 1-phenyltetradecyl group.

As an alkenyl group, straight-chain, branched-chain or cyclic alkenyl groups having, for example, 2 to 50 carbon atoms, preferably 2 to 30 carbon atoms, more preferably 2 to 20 carbon atoms can be recited, and concrete examples include a vinyl group, a 1-propenyl group, a 2-propenyl group, a 2-butenyl group, a 2-pentenyl group, a 2-hexenyl group, a 2-heptenyl group, a 2-octenyl group, a 2-nonenyl group, a 2-icocenyl group, a 1-cyclohexenyl group and a 1-cycloheptenyl group.

As an alkynyl group, straight-chain or branched-chain alkynyl groups having, for example, 2 to 50 carbon atoms, preferably 2 to 30 carbon atoms, more preferably 2 to 20 carbon atoms can be recited, and concrete examples include an ethynyl group, a 1-propynyl group, a 2-propynyl group, a 2-butynyl group, a 2-pentynyl group, a 2-hexynyl group, a 2-heptynyl group, a 2-octynyl group, a 2-nonynyl group, and a 2-icosynyl.

As a heterocyclic group, aliphatic heterocyclic groups and aromatic heterocyclic groups can be recited. As an aliphatic heterocyclic group, 3 to 8-membered, preferably 4 to 6-membered monocyclic aliphatic heterocyclic groups, polycyclic or condensed cyclic aliphatic heterocyclic groups having, for example, 2 to 14 carbon atoms, and containing at least one, preferably one to three heteroatoms such as a nitrogen atom, an oxygen atom and/or a sulfur atom as a heteroatom can be recited. Concrete examples of an aliphatic heterocyclic group include a 2-pyrrolidyl group, a 2-piperidinyl group, a 2-piperadinyl group, a 2-morpholinyl group, a 2-tetrahydrofuryl group, a 2-tetrahydropyranyl group and a 2-tetrahydrothienyl group.

As an aromatic heterocyclic group, 5 or 6-membered monocyclic heteroaryl groups, polycyclic or condensed cyclic heteroaryl groups having, for example, 2 to 15 carbon atoms, and containing at least one, preferably one to three heteroatoms such as a nitrogen atom, an oxygen atom and/or a sulfur atom as a heteroatom can be recited. Concrete examples include a 2-furyl group, a 3-furyl group, a 2-thienyl group, a 3-thienyl group, a 2-pyridyl group, a 3-pyridyl group, a 2-pyrimidyl group, a 2-pyrazyl group, a 2-imidazolyl group, a 4-imidazolyl group, a 2-oxazolyl group, a 2-thiazolyl group, a 2-benzfuryl group, a 3-benzfuryl group, a 2-benzthienyl group, a 3-benzthienyl group, a 2-quinolyl group, a 3-quinolyl group, a 1-isoquinolyl group, a 2-benzimidazolyl group, a 2-benzoxazolyl group and a 2-benzthiazolyl group.

As a carbonyl group having one monovalent group, those represented by the following general formula (A) can be recited:

[Chemical Formula 12]

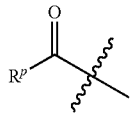
(A)

(in the general formula (A), $R^P$ represents a monovalent group, concretely a hydrogen atom, an alkyl group, an aryl group, an aralkyl group, an alkenyl group, an alkynyl group, a heterocyclic group, an alkoxy group, an aryloxy group, an aralkyloxy group, an amino group, a halogeno group or a halogenoalkyl group, and among these groups, an alkyl group, an aryl group, an aralkyl group, an alkenyl group, an alkynyl group, a heterocyclic group, an alkoxy group, an aryloxy group, an aralkyloxy group and a halogenoalkyl group may have substituent(s).)

Description will be made for $R^P$ in the general formula (A). As an alkyl group, an aryl group, an aralkyl group, an alkenyl group, an alkynyl group, and a heterocyclic group, the same groups as those specifically described above in this section can be recited.

As an alkoxy group, straight-chain, branched-chain or cyclic alkoxy groups made up of an alkyl group having 1 to 50 carbon atoms, preferably 1 to 30 carbon atoms, more preferably 1 to 20 carbon atoms can be recited, and concrete examples include a methoxy group, an ethoxy group, an n-propoxy group, an isopropoxy group, an n-butoxy group, an isobutoxy group, a s-butoxy group, a tert-butoxy group, an n-pentyloxy group, an n-hexyloxy group, an n-heptyloxy group, an n-octyloxy group, an n-nonyloxy group, an n-decyloxy group, an n-undecyloxy group, an n-dodecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group, an n-icosyloxy group, a cyclopropyloxy group, a cyclopentyloxy group and a cyclohexyloxy group.

As an aryloxy group, aryloxy groups made up of a monocyclic, polycyclic or condensed cyclic aryl group having 6 to 36 carbon atoms, preferably 6 to 18 carbon atoms, more preferably 6 to 14 carbon atoms can be recited, and concrete examples include a phenoxy group, a p-methylphenoxy group and a 1-naphtyloxy group.

As an aralkyloxy group, groups in which at least one hydrogen atom in the aforementioned alkyl group of the alkoxy group is substituted by the aforementioned aryl group can be recited, and aralkyloxy groups having, for example, 7 to 15 carbon atoms are preferred, and concrete examples include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphtylmethoxy group and a 2-naphtylmethoxy group.

An amino group may have substituent(s), for example, an amino group in which at least one hydrogen atom in the amino group is each independently substituted by an alkyl group aforementioned in this section, an aryl group aforementioned in this section, an alkenyl group aforementioned in this section, an alkynyl group aforementioned in this section or an aralkyl group aforementioned in this section can be recited, and concrete examples include an N,N-diethylamino group, an N,N-diisopropylamino group, an N,N-dibutylamino group, an N,N-dipentylamino group, an N,N-didecylamino group, an N,N-dicyclohexylamino group, an N,N-diphenyamino group, an N-naphtyl-N-phenylamino group and an N,N-dibenzylamino group. Also when the group has two substituents, they may bind to each other to form a ring, and concrete examples of such a group include a 1-pyrrolidinyl group and a 1-piperidinyl group. Also a 1-piperadinyl group and a 1-morpholinyl group can be recited as an amino group.

As a halogeno group, a fluoro group, a chloro group, a bromo group and an iodo group can be recited.

As a halogenoalkyl group, groups in which at least one hydrogen atom on the aforementioned alkyl group is substituted by a halogen atom can be recited, and concrete examples include a trifluoromethyl group and an n-nonafluorobutyl group, and more concrete examples include a trifluoromethyl group.

When $R^P$ is an alkyl group, an aryl group, an aralkyl group, an alkenyl group, an alkynyl group, a heterocyclic group, an alkoxy group, an aryloxy group, an aralkyloxy group or a halogenoalkyl group, it may have substituent(s).

As a substituent that can be possessed when $R^P$ is an alkyl group, an aralkyl group, an alkenyl group, an alkynyl group or a halogenoalkyl group, a heterocyclic group, a hydroxyl group, an oxo group, an alkoxy group, an aryloxy group, an aralkyloxy group, an amino group, a halogeno group, a silyl group, a siloxy group and acyloxy group can be recited. Among these groups, as a heterocyclic group, an alkoxy group, an aryloxy group, an aralkyloxy group, an amino group and a halogeno group, the same groups as those described above in this section can be recited.

As a silyl group, groups in which at least one hydrogen atom on a silyl group is substituted by the alkyl group aforementioned in this section, the aryl group aforementioned in this section, the aralkyl group aforementioned in this section can be recited. Concrete examples include a trimethylsilyl group, a triethylsilyl group, a triisopropylsilyl group, a t-butyldimethylsilyl group, a t-butyldiphenylsilyl group and a triphenylsilyl group.

As a siloxy group, groups in which a silyl group aforementioned in this section binds to an oxygen atom can be recited, and concrete examples include a trimethylsiloxy group, a triethylsiloxy group, a triisopropylsiloxy group, a t-butyldimethylsiloxy group, a t-butyldiphenylsiloxy group and a triphenylsiloxy group.

As an acyloxy group, straight-chain, branched-chain or cyclic acyloxy groups having 1 to 50 carbon atoms, preferably 1 to 30 carbon atoms, more preferably 2 to 20 carbon atoms can be recited, and concrete examples include an acetoxy group, a benzyloxy group, a pivaloyloxy group (2,2-dimethylpropanoyloxy group), an n-butanoyloxy group, an n-pentanoyloxy group, an n-hexanoyloxy group, an n-heptanoyloxy group, an n-octanoyloxy group, an n-nonanoyloxy group, an n-decanoyloxy group, an n-undecanoyloxy group and an n-dodecanoyloxy group.

As a substituent that can be possessed when $R^P$ is an aryl group, a heterocyclic group, an alkoxy group, an aryloxy group or an aralkyloxy group, an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group and an acyloxy group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group and an acyloxy group, the same groups as those described above in this section can be recited.

In the scheme (9), these alkyl group, aryl group, aralkyl group, alkenyl group, alkynyl group and heterocyclic group may have substituent(s).

As a substituent that can be possessed by an alkyl group, an aralkyl group, an alkenyl group and an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group can be recited. Among these groups, as a heterocyclic group, an alkoxy group, an aryloxy group, an aralkyloxy group, an amino group, a halogeno group, a silyl group, a siloxy group, an acyloxy group and a carbonyl group, the same groups as those described above in this section can be recited.

As a substituent that can be possessed by an aryl group and a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group, the same groups as those described above in this section can be recited.

When $R^{13}$ and $R^{14}$ bind to each other to form a ring together with the adjacent atom, ketones form cyclic ketones.

When $R^{13}$ and $R^{14}$ each independently represent a carbonyl group having one monovalent group, an alkenyl group or an alkynyl group, or when $R^{13}$ and $R^{14}$ each independently have a carbonyl group having one monovalent group, an alkenyl group, an alkynyl group and/or an acyloxy group as a substituent, these groups may be reduced in the reaction process.

When $R^{13}$ and $R^{14}$ each independently have an aralkyloxy group as a substituent, the aralkyloxy group may be reduced in the reaction process.

When PNP and/or NHC represented by the aforementioned general formula (2) are/is an optically active form, alcohol in which either one of the enantiomers is excessive may be obtained as a product in the scheme (9).

While the hydrogenation reaction from ketones to alcohols in the present invention can be preferably conducted in the absence or in the presence of solvent(s), it is desirable to use solvent(s). Examples of a preferred solvent include aromatic hydrocarbons such as toluene, and xylene, aliphatic hydrocarbons such as hexane and heptane, halogenated hydrocarbons such as methylene chloride and chlorobenzene, ethers such as diethyl ether, tetrahydrofuran, methyl tert-butyl ether, and cyclopentyl methyl ether, alcohols such as methanol, ethanol, isopropyl alcohol, n-butyl alcohol, 2-butanol, and tert-butyl alcohol, polyalcohols such as ethylene glycol, propylene glycol, 1,2-propane diol, and glycerin and water, and concrete examples of a particularly preferred solvent include toluene, tetrahydrofuran and methanol. These solvents may be used solely or in combination of two or more kinds.

While the use amount of the solvent is not particularly limited as long as the reaction proceeds, it is appropriately selected in the range of normally 0.001 mol/L (substance amount of substrate/solvent amount) to 20 mol/L, preferably 0.005 mol/L to 15 mol/L, more preferably 0.01 mol/L to 10 mol/L. The reaction is conducted under stirring as needed.

As a hydrogen donor used in the method of the present invention, hydrogen gas, formic acid, a primary alcohol, and a secondary alcohol can be recited. Preferred concrete examples include hydrogen gas, methanol, ethanol, 1-butanol and isopropanol, and more preferred concrete examples include hydrogen gas.

While the use amount of the catalyst varies depending on the substrate, the reaction condition, the kind of the catalyst and so on, it is normally within the range of 0.0001 mol % to 20 mol % (the amount of substance of the ruthenium complex to the amount of substance of the substrate), preferably within the range of 0.002 mol % to 10 mol %, more preferably within the range of 0.005 mol % to 5 mol %.

In hydrogenation of ketones of the present invention, additive(s) may be added appropriately. As the additive, for example, a salt of Brønsted acid, a basic compound and so on can be recited. As a salt of Brønsted acid, for example, metal salts formed of Brønsted acid can be recited, and preferably, metal halides and the like can be recited. More preferred concrete examples include lithium chloride, lithium bromide, lithium iodide, sodium fluoride, sodium bromide, sodium iodide, potassium fluoride and potassium bromide. Examples of a basic compound include amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine and N-methylmorpholine, alkali metal carbonates such as potassium carbonate, sodium carbonate, lithium carbonate, and cesium carbonate, alkaline earth metal carbonates such as magnesium carbonate and calcium carbonate, alkali metal hydrogen carbonates such as sodium hydrogen carbonate and potassium hydrogen carbonate, alkali metal hydroxides such as sodium hydroxide and potassium hydroxide and lithium hydroxide, alkaline earth metal hydroxides such as magnesium hydroxide and calcium hydroxide, alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide and lithium tert-butoxide, alkaline earth metal alkoxides such as magnesium methoxide and magnesium ethoxide, and metal hydrides such as sodium hydride, calcium hydride, lithium borohydride, sodium borohydride, potassium borohydride and aluminum lithium hydride, and particularly preferred concrete examples include sodium methoxide, potassium tert-butoxide and sodium hydrogen bromide. Also, NHC and an equivalent thereof may be added as an additive. While the use amount of such an additive is not particularly limited as long as the reaction proceeds, use of the additive in an amount of not more than 10 mol % of the substrate can afford sufficiently high degree of conversion.

The present reaction is desirably conducted in an inert gas atmosphere, hydrogen gas atmosphere, carbon monoxide gas atmosphere or an air atmosphere. As an inert gas, concretely, argon gas, nitrogen gas and the like can be recited. These gases and atmospheric air may be used individually or used as a mixed gas.

The pressure in conducting hydrogenation using hydrogen gas as a hydrogen donor is normally between atmospheric pressure and 20 MPa, preferably between atmospheric pressure and 10 MPa, more preferably between atmospheric pressure and 5 MPa. The atmospheric pressure means the pressure under a hydrogen gas atmosphere where pressurization of hydrogen gas is not required.

The reaction temperature is appropriately selected normally in the range of −50° C. to 200° C., preferably in the range of −20° C. to 150° C., more preferably in the range of 0° C. to 100° C.

While the reaction time naturally varies depending on the solvent, the reaction temperature and other conditions, it is appropriately selected normally in the range of 1 minute to 72 hours, preferably in the range of 1 minute to 24 hours, more preferably in the range of 5 minutes to 12 hours.

The product may be subject to a post treatment, isolation and purification as needed. As a method of a post treatment, for example, concentration, washing, extraction, backward extraction, and crystallization by addition of a poor solvent can be recited, and these may be conducted solely or in combination. As a method for isolation and purification, for example, drying up of a reaction solution, various kinds of chromatography, distillation, recrystallization and washing of crystals with a poor solvent can be recited, and these may be conducted solely or in combination.

Subsequently, a method for producing alcohols by hydrogenation of aldehydes will be described.

The method for producing alcohols by hydrogenation of aldehydes in the present invention is a method for producing alcohols from aldehydes using a ruthenium complex represented by the general formula (1) and a hydrogen donor, and for example, a method for producing alcohols from aldehydes represented by the following scheme (10) can be recited:

[Chemical Formula 13]

(10)

(in the scheme (10), $R^{15}$ represents an alkyl group, an aryl group, an aralkyl group, an alkenyl group, an alkynyl group, a heterocyclic group or a carbonyl group having one monovalent group, and preferably represents an alkyl group, an aryl group. Also, these alkyl group, aryl group, aralkyl group, alkenyl group, alkynyl group and heterocyclic group may have substituent (s).)

Description will be made for $R^{15}$ in the scheme (10). As an alkyl group, an aryl group, an aralkyl group, an alkenyl group, an alkynyl group, a heterocyclic group and a carbonyl group having one monovalent group, the same groups as specifically described in the description of $R^{13}$ and $R^{14}$ in the aforementioned scheme (9) can be recited.

Among these groups, an alkyl group, an aryl group, an aralkyl group, an alkenyl group, an alkynyl group and a heterocyclic group may have substituent(s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

When $R^{15}$ is a carbonyl group having one monovalent group, an alkenyl group or an alkynyl group, or when $R^{15}$ has a carbonyl group having one monovalent group, an alkenyl group, an alkynyl group and/or an acyloxy group as a substituent, these groups may be reduced in the reaction process.

When $R^{15}$ has an aralkyloxy group as a substituent, the aralkyloxy group may be reduced in the reaction process.

While the hydrogenation of aldehydes of the present invention can be preferably conducted in the absence or in the presence of solvent(s), it is desired to use solvent(s). The solvent and the use amount of the solvent can be the same as the solvent and the use amount of the solvent as specifically described in the hydrogenation of ketones.

As a hydrogen donor used in the hydrogenation of aldehydes of the present invention, the same hydrogen donor as the hydrogen donor specifically described in the hydrogenation of ketones can be recited.

Also, in the hydrogenation of aldehydes of the present invention, additive(s) may be added appropriately. As the additive, the same additive as the additive specifically described in the hydrogenation of ketones can be recited.

The present reaction is desirably conducted in an inert gas atmosphere, hydrogen gas atmosphere, carbon monoxide gas atmosphere or air atmosphere. As an inert gas, concretely, argon gas, nitrogen gas and the like can be recited. These gases and atmospheric air may be used individually or used as a mixed gas.

The pressure in conducting hydrogenation using hydrogen gas as a hydrogen donor is normally between atmospheric pressure and 20 MPa, preferably between atmospheric pressure and 10 MPa, more preferably between atmospheric pressure and 5 MPa. The atmospheric pressure means the pressure under a hydrogen gas atmosphere where pressurization of hydrogen gas is not required.

The reaction temperature is appropriately selected normally in the range of −50° C. to 200° C., preferably in the range of −20° C. to 150° C., more preferably in the range of 0° C. to 100° C.

While the reaction time naturally varies depending on the solvent, the reaction temperature and other conditions, it is appropriately selected normally in the range of 1 minute to 72 hours, preferably in the range of 1 minute to 24 hours, more preferably in the range of 5 minutes to 12 hours.

The product may be subject to a post treatment, isolation and purification as needed. As a method of a post treatment, for example, concentration, washing, extraction, backward extraction, and crystallization by addition of a poor solvent can be recited, and these may be conducted solely or in combination. As a method for isolation and purification, for example, drying up of a reaction solution, various kinds of chromatography, distillation, recrystallization and washing of crystals with a poor solvent can be recited, and these may be conducted solely or in combination.

Subsequently, a method for producing alcohols, aldehydes and hemiacetals by hydrogenation of esters will be described.

As a method for producing alcohols, aldehydes and hemiacetals by hydrogenation of esters in the present invention, a method represented by the following scheme (11) can be recited:

[Chemical Formula 14]

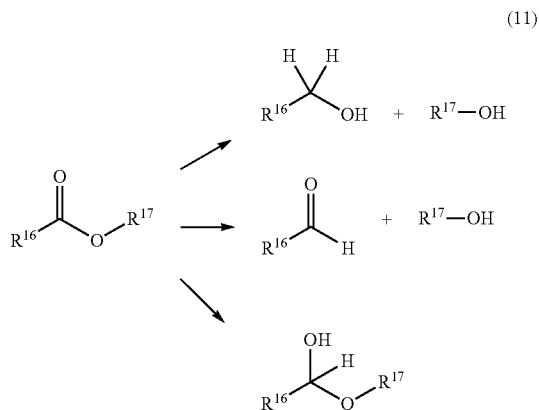

(11)

(in the scheme (11), $R^{16}$ represents a hydrogen atom, an alkyl group, an aryl group, an aralkyl group, an alkenyl group, an alkynyl group, a heterocyclic group or a carbonyl group having one monovalent group, preferably represents an alkyl group, an aryl group or a heterocyclic group. Among these groups, an alkyl group, an aryl group, an aralkyl group, an alkenyl group, an alkynyl group and a heterocyclic group may have substituent(s). $R^{17}$ represents an alkyl group, an aryl group, an aralkyl group, an alkenyl group, an alkynyl group or a heterocyclic group, and preferably represents an alkyl group. Also, these alkyl group, aryl group, aralkyl group, alkenyl group, alkynyl group and heterocyclic group may have substituent (s). $R^{16}$ and $R^{17}$ may bind to each other.)

As an alkyl group, an aryl group, an aralkyl group, an alkenyl group, an alkynyl group, a heterocyclic group and a carbonyl group having one monovalent group in $R^{16}$ in the scheme (11), the same groups as specifically described in the description of $R^{13}$ and $R^{14}$ in the aforementioned scheme (9) can be recited.

Among these groups, an alkyl group, an aryl group, an aralkyl group, an alkenyl group, an alkynyl group and a heterocyclic group may have substituent(s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

As an alkyl group, an aryl group, an aralkyl group, an alkenyl group, an alkynyl group and a heterocyclic group in $R^{17}$ in the scheme (11), the same groups as specifically described in the description of $R^{13}$ and $R^{14}$ in the aforementioned scheme (9) can be recited.

These groups may have substituent(s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

When $R^{16}$ and $R^{17}$ bind to each other, esters form cyclic compounds such as lactone.

When $R^{16}$ is a carbonyl group having one monovalent group, or when $R^{16}$ and $R^{17}$ each independently have a carbonyl group having one monovalent group as a substituent, the carbonyl group having one monovalent group may be reduced in the reaction process.

When $R^{16}$ and $R^{17}$ each independently represent an alkenyl group or an alkynyl group, or when $R^{16}$ and $R^{17}$ each independently have an alkenyl group, an alkynyl group and/or an acyloxy group as a substituent, these groups may be reduced in the reaction process.

When $R^{16}$ and $R^{17}$ each independently have an aralkyloxy group as a substituent, the aralkyloxy group may be reduced in the reaction process.

When $R^{16}$ and $R^{17}$ bind to each other, esters form cyclic compounds such as lactone.

While the hydrogenation of esters of the present invention can be preferably conducted in the absence or in the presence of solvent(s), it is desired to use solvent(s). The solvent and the use amount of the solvent can be the same as the solvent and the use amount of the solvent as specifically described in the hydrogenation of ketones.

As a hydrogen donor used in the hydrogenation of esters of the present invention, the same hydrogen donor as the hydrogen donor specifically described in the hydrogenation of ketones can be recited.

Also, in the hydrogenation of esters of the present invention, additive(s) may be added appropriately. As the additive, the same additive as the additive specifically described in the hydrogenation of ketones can be recited.

The present reaction is desirably conducted in an inert gas atmosphere, hydrogen gas atmosphere, carbon monoxide gas atmosphere or air atmosphere. As an inert gas, concretely, argon gas, nitrogen gas and the like can be recited. These gases and atmospheric air may be used individually or used as a mixed gas.

The pressure in conducting hydrogenation using hydrogen gas as a hydrogen donor is normally between atmospheric pressure and 20 MPa, preferably between atmospheric pressure and 10 MPa, more preferably between atmospheric pressure and 5 MPa. The atmospheric pressure means the pressure under a hydrogen gas atmosphere where pressurization of hydrogen gas is not required.

The reaction temperature is appropriately selected normally in the range of −50° C. to 200° C., preferably in the range of −20° C. to 150° C., more preferably in the range of 0° C. to 100° C.

While the reaction time naturally varies depending on the solvent, the reaction temperature and other conditions, it is appropriately selected normally in the range of 1 minute to 72 hours, preferably in the range of 1 minute to 24 hours, more preferably in the range of 5 minutes to 12 hours.

The product may be subject to a post treatment, isolation and purification as needed. As a method of a post treatment, for example, concentration, washing, extraction, backward extraction, and crystallization by addition of a poor solvent can be recited, and these may be conducted solely or in combination. As a method for isolation and purification, for example, drying up of a reaction solution, various kinds of chromatography, distillation, recrystallization and washing of crystals with a poor solvent can be recited, and these may be conducted solely or in combination.

Subsequently, a method for producing alcohols, aldehydes, amines and hemiaminals by hydrogenation of amides will be described.

As a method for producing alcohols, aldehydes, amines and hemiaminals by hydrogenation of amides in the present invention, a method represented by the following scheme (12) can be recited:

[Chemical Formula 15]

[Chemical Formula 15]

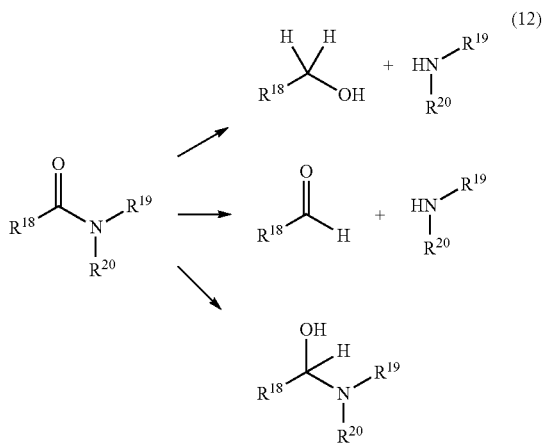

(in the scheme (12), $R^{18}$ represents a hydrogen atom, an alkyl group, an aryl group, an aralkyl group, an alkenyl group, an alkynyl group, a heterocyclic group or a carbonyl group having one monovalent group, preferably represents an alkyl group, an aryl group, and further preferably represents an aryl group. Among these groups, an alkyl group, an aryl group, an aralkyl group, an alkenyl group, an alkynyl group and a heterocyclic group may have substituent(s). $R^{19}$ and $R^{20}$ each independently represent a hydrogen atom, an alkyl group, an aryl group, an aralkyl group, an alkenyl group, an alkynyl group or a heterocyclic group, preferably represent an alkyl group, an aryl group, an aralkyl group, and further preferably represent an alkyl group. These alkyl group, aryl group, aralkyl group, alkenyl group, alkynyl group and heterocyclic group may have substituent(s). $R^{18}$ and $R^{19}$ and/or $R^{20}$, or $R^{19}$ and $R^{20}$ may bind to each other.)

As an alkyl group, an aryl group, an aralkyl group, an alkenyl group, an alkynyl group, a heterocyclic group and a carbonyl group having one monovalent group in $R^{18}$ in the scheme (12), the same groups as specifically described in the description of $R^{13}$ and $R^{14}$ in the aforementioned scheme (9) can be recited.

Among these groups, an alkyl group, an aryl group, an aralkyl group, an alkenyl group, an alkynyl group and a heterocyclic group may have substituent(s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

As an alkyl group, an aryl group, an aralkyl group, an alkenyl group, an alkynyl group and a heterocyclic group in $R^{19}$ and $R^{20}$ in the scheme (12), the same groups as specifically described in the description of $R^{13}$ and $R^{14}$ in the aforementioned scheme (9) can be recited. These groups may have substituent (s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

When $R^{18}$ is a carbonyl group having one monovalent group, or when $R^{18}$, $R^{19}$ and $R^{20}$ each independently have a carbonyl group having one monovalent group as a substituent, the carbonyl group having one monovalent group may be reduced in the reaction process.

When $R^{18}$, $R^{19}$ and $R^{20}$ each independently represent an alkenyl group or an alkynyl group, or when $R^{18}$, $R^{19}$ and $R^{20}$ each independently have an alkenyl group, an alkynyl group and/or an acyloxy group as a substituent, these groups may be reduced in the reaction process.

When $R^{18}$, $R^{19}$ and $R^{20}$ each independently have an aralkyloxy group as a substituent, the aralkyloxy group may be reduced in the reaction process.

When $R^{18}$ and $R^{19}$ and/or $R^{20}$ bind to each other, amides form cyclic compounds such as lactam. When $R^{19}$ and $R^{20}$ bind to each other, amides form amides of cyclic amine.

While the hydrogenation of amides of the present invention can be preferably conducted in the absence or in the presence of solvent(s), it is desired to use solvent(s). The solvent and the use amount of the solvent can be the same as the solvent and the use amount of the solvent as specifically described in the hydrogenation of ketones.

As a hydrogen donor used in the hydrogenation of amides of the present invention, the same hydrogen donor as the hydrogen donor specifically described in the hydrogenation of ketones can be recited.

Also, in the hydrogenation of amides of the present invention, additive(s) may be added appropriately. As the additive, the same additive as the additive specifically described in the hydrogenation of ketones can be recited.

The present reaction is desirably conducted in an inert gas atmosphere, hydrogen gas atmosphere, carbon monoxide gas atmosphere or air atmosphere. As an inert gas, concretely, argon gas, nitrogen gas and the like can be recited. These gases and atmospheric air may be used individually or used as a mixed gas.

The pressure in conducting hydrogenation using hydrogen gas as a hydrogen donor is normally between atmospheric pressure and 20 MPa, preferably between atmospheric pressure and 10 MPa, more preferably between atmospheric pressure and 5 MPa. The atmospheric pressure means the pressure under a hydrogen gas atmosphere where pressurization of hydrogen gas is not required.

The reaction temperature is appropriately selected normally in the range of −50° C. to 200° C., preferably in the range of −20° C. to 150° C., more preferably in the range of 0° C. to 100° C.

While the reaction time naturally varies depending on the solvent, the reaction temperature and other conditions, it is appropriately selected normally in the range of 1 minute to 72 hours, preferably in the range of 1 minute to 24 hours, more preferably in the range of 5 minutes to 12 hours.

The product may be subject to a post treatment, isolation and purification as needed. As a method of a post treatment, for example, concentration, washing, extraction, backward extraction, and crystallization by addition of a poor solvent can be recited, and these may be conducted solely or in combination. As a method for isolation and purification, for example, drying up of a reaction solution, various kinds of chromatography, distillation, recrystallization and washing of crystals with a poor solvent can be recited, and these may be conducted solely or in combination.

Next, a method for producing carbonyl compounds by oxidation of alcohols, hemiacetals, and hemiaminals will be described.

As a method for producing carbonyl compounds by dehydrogenation of alcohols, hemiacetals and hemiaminals in the present invention, a method represented by the following schemes (13), (14) and (15) can be recited:

[Chemical Formula 16]

(13)

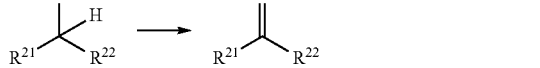

(14)

(15)

(in the schemes (13), (14) and (15), $R^{21}$, $R^{22}$, $R^{23}$, $R^{25}$ each independently represent a hydrogen atom, an alkyl group, an aryl group, an aralkyl group, an alkenyl group, an alkynyl group, a heterocyclic group, an alkoxy group, an aryloxy group, an aralkyloxy group or a carbonyl group having one monovalent group, preferably represent an alkyl group, an aryl group, an aralkyl group, an alkenyl group, an alkynyl group, or a heterocyclic group, more preferably represent an alkyl group, an aryl group. These alkyl group, aryl group, aralkyl group, alkenyl group, alkynyl group, heterocyclic group, alkoxy group, aryloxy group and aralkyloxy group may have substituent(s). $R^{24}$ represents an alkyl group, an aryl group, an aralkyl group, an alkenyl group, an alkynyl group or a heterocyclic group. These alkyl group, aryl group, aralkyl group, alkenyl group, alkynyl group and heterocyclic group may have substituent(s). $R^{26}$ and $R^{27}$ each independently represent a hydrogen atom, an alkyl group, an aryl group, an aralkyl group, an alkenyl group, an alkynyl group or a heterocyclic group, and these alkyl group, aryl group, aralkyl group, alkenyl group, alkynyl group and heterocyclic group may have substituent(s). $R^{21}$ and $R^{22}$ in the scheme (13) may bind to each other, $R^{23}$ and $R^{24}$ in the scheme (14) may bind to each other, and $R^{25}$ and $R^{26}$ and/or $R^{27}$, or $R^{27}$ and $R^{26}$ in the scheme (15) may bind to each other.)

As an alkyl group, an aryl group, an aralkyl group, an alkenyl group, an alkynyl group, a heterocyclic group, an alkoxy group, an aryloxy group, an aralkyloxy group and a carbonyl group having one monovalent group in $R^{21}$, $R^{22}$, $R^{23}$ and $R^{25}$ in the schemes (13), (14) and (15), the same groups as specifically described in the description of $R^{13}$ and $R^{14}$ in the aforementioned scheme (9) can be recited.

Among these groups, an alkyl group, an aryl group, an aralkyl group, an alkenyl group, an alkynyl group, a heterocyclic group, an alkoxy group, an aryloxy group and an aralkyloxy group may have substituent(s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group, a heterocyclic group, an alkoxy group, an aryloxy group or an aralkyloxy group, an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

Description will be made for $R^{24}$ in the scheme (14).

As an alkyl group, an aryl group, an aralkyl group, an alkenyl group, an alkynyl group and a heterocyclic group, the same groups as specifically described in the description of $R^{13}$ and $R^{14}$ in the aforementioned scheme (9) can be recited. These groups may have substituent(s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

When $R^{21}$ and $R^{22}$ in the scheme (13) bind to each other, alcohols form cyclic compounds such as cyclic alcohol. When $R^{23}$ and $R^{24}$ in the scheme (14) bind to each other, hemiacetals form cyclic compounds. When $R^{25}$ and $R^{26}$ and/or $R^{27}$ in the scheme (15) bind to each other, hemiaminals form cyclic compounds. When $R^{26}$ and $R^{27}$ bind to each other, hemiaminals form cyclic compounds.

In the scheme (13) to the scheme (15), when $R^{21}$ to $R^{27}$ each independently have a hydroxyl group as a substituent, the hydroxyl group may be oxidized in the reaction process.

The hemiacetals in the scheme (14) may be formed in a reaction system, and for example, a technique represented by the following scheme (14') can be recited:

[Chemical Formula 17]

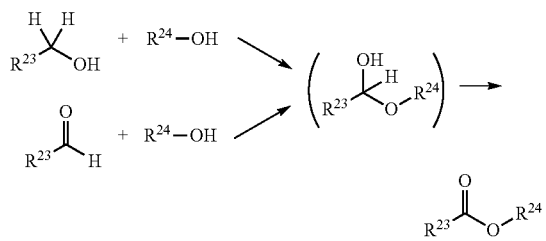

(14')

(in the scheme (14'), $R^{23}$ and $R^{24}$ represent groups having the same definition as in the scheme (14).)

The hemiaminals in the scheme (15) may be formed in a reaction system, and for example, a technique represented by the following scheme (15') can be recited:

[Chemical Formula 18]

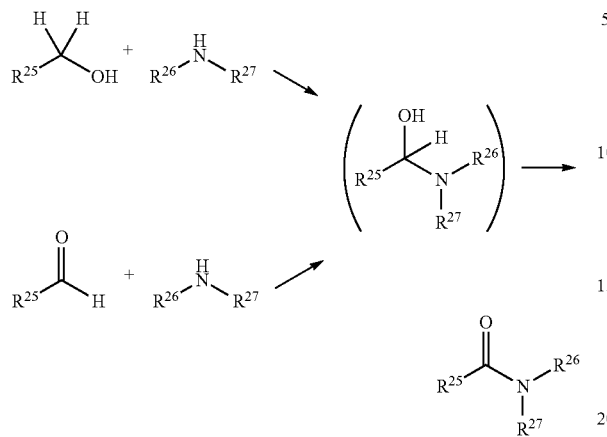

(in the scheme (15'), $R^{25}$, $R^{26}$ and $R^{27}$ represent groups having the same definition as in scheme (15).)

While the dehydrogenation of alcohols, hemiacetals and hemiaminals of the present invention can be preferably conducted in the absence or in the presence of solvent(s), it is desired to use solvent(s). Preferred solvents include aromatic hydrocarbons such as toluene, and xylene, aliphatic hydrocarbons such as hexane, and heptane, halogenated hydrocarbons such as methylene chloride, and chlorobenzene, ethers such as diethyl ether, tetrahydrofuran, methyl tert-butyl ether, and cyclopentyl methyl ether, and ketones such as 1-phenylethanone and benzphenone, and more preferred concrete examples include toluene and xylene.

While the use amount of the solvent is not particularly limited as long as the reaction proceeds, it is appropriately selected in the range of normally 0.001 mol/L (substance amount of substrate/solvent amount) to 20 mol/L, preferably 0.005 mol/L to 15 mol/L, more preferably 0.01 mol/L to 10 mol/L. The reaction is conducted under stirring as needed.

Also, in the dehydrogenation of alcohols, hemiacetals and hemiaminals of the present invention, additive(s) may be added appropriately. As the additive, the same additive as the additive specifically described in the hydrogenation of ketones can be recited.

The present reaction is desirably conducted in an inert gas atmosphere, or air atmosphere. As an inert gas, concretely, argon gas, nitrogen gas and the like can be recited. These inert gas and atmospheric air may be used individually or used as a mixed gas.

The reaction temperature is appropriately selected normally in the range of −50° C. to 300° C., preferably in the range of 0° C. to 200° C., more preferably in the range of 20° C. to 150° C.

While the reaction time naturally varies depending on the solvent, the reaction temperature and other conditions, it is appropriately selected normally in the range of 1 minute to 72 hours, preferably in the range of 1 minute to 24 hours, more preferably in the range of 5 minutes to 12 hours.

The product may be subject to a post treatment, isolation and purification as needed. As a method of a post treatment, for example, concentration, washing, extraction, backward extraction, and crystallization by addition of a poor solvent can be recited, and these may be conducted solely or in combination. As a method for isolation and purification, for example, drying up of a reaction solution, various kinds of chromatography, distillation, recrystallization and washing of crystals with a poor solvent can be recited, and these may be conducted solely or in combination.

Subsequently, a method for producing N-alkylamine compounds via condensation between alcohols and amines will be described.

The method for producing N-alkylamine compounds via condensation between alcohols and amines in the present invention is represented, for example, by the following schemes (16) and (17):

[Chemical Formula 19]

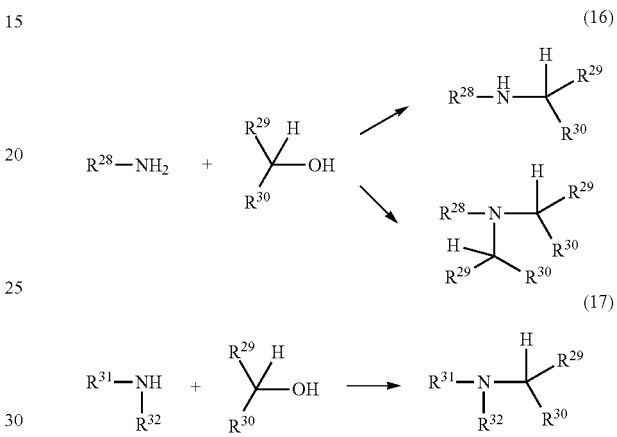

(in the schemes (16) and (17), $R^{28}$, $R^{31}$ and $R^{32}$ each independently represent a hydrogen atom, an alkyl group, an aryl group, an aralkyl group, an alkenyl group, an alkynyl group or a heterocyclic group, preferably represent an alkyl group, an aryl group, more preferably represent an aryl group. Among these groups, an alkyl group, an aryl group, an aralkyl group, an alkenyl group, an alkynyl group and a heterocyclic group may have substituent(s). $R^{29}$ and $R^{30}$ each independently represent a hydrogen atom, an alkyl group, an aryl group, an aralkyl group, an alkenyl group, an alkynyl group, a heterocyclic group, a halogeno group, a halogenoalkyl group or a silyl group, and preferably represent an alkyl group or an aralkyl group. Among these groups, an alkyl group, an aryl group, an aralkyl group, an alkenyl group, an alkynyl group, a heterocyclic group and a halogenoalkyl group may have substituent(s).

Also, $R^{28}$ and $R^{29}$, $R^{28}$ and $R^{30}$, $R^{28}$ and $R^{29}$ and $R^{30}$, or $R^{29}$ and $R^{30}$ in the scheme (16) may bind to each other, and $R^{29}$ and $R^{30}$, $R^{32}$ and $R^{31}$, $R^{32}$ and $R^{30}$ and/or $R^{29}$, $R^{32}$ and $R^{31}$ and $R^{30}$ and/or $R^{29}$, or $R^{31}$ and $R^{30}$ and/or $R^{29}$ in the scheme (17) may bind to each other.)

As an alkyl group, an aryl group, an aralkyl group, an alkenyl group, an alkynyl group and a heterocyclic group in $R^{28}$, $R^{31}$ and $R^{32}$ in the schemes (16) and (17), the same groups as specifically described in the description of $R^{13}$ and $R^{14}$ in the aforementioned scheme (9) can be recited. Among these groups, an alkyl group, an aryl group, an aralkyl group, an alkenyl group, an alkynyl group and a heterocyclic group may have substituent(s).

As a substituent that can be possessed by an alkyl group, an aralkyl group, an alkenyl group or an alkynyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

As an alkyl group, an aryl group, an aralkyl group, an alkenyl group, an alkynyl group, a heterocyclic group, a halogeno group, a halogenoalkyl group and a silyl group in $R^{29}$ and $R^{30}$ in the schemes (16) and (17), the same groups as specifically described in the description of $R^{13}$ and $R^{14}$ in the aforementioned scheme (9) can be recited. Among these groups, an alkyl group, an aryl group, an aralkyl group, an alkenyl group, an alkynyl group, a heterocyclic group and a halogenoalkyl group may have substituent(s). As a substituent that can be possessed by an alkyl group, an aralkyl group, an alkenyl group, an alkynyl group or a halogenoalkyl group, a heterocyclic group, a hydroxyl group, an alkoxy group, an aryloxy group, an aralkyloxy group, an amino group, a halogeno group, a silyl group, a siloxy group, an acyloxy group and a carbonyl group having one monovalent group can be recited. Among these groups, as a heterocyclic group, an alkoxy group, an aryloxy group, an aralkyloxy group, an amino group, a halogeno group, a silyl group, a siloxy group, an acyloxy group and a carbonyl group having one monovalent group, the same groups as specifically described in the description of $R^{13}$ and $R^{14}$ in the aforementioned scheme (9) can be recited.

As a substituent that can be possessed by an aryl group or a heterocyclic group, an alkyl group, an aryl group, anaralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group and a carbonyl group having one monovalent group can be recited. Among these groups, as an alkyl group, an aryl group, an aralkyl group, an alkenyl group, an alkynyl group, a heterocyclic group, an alkoxy group, an aryloxy group, an aralkyloxy group, an amino group, a halogeno group, a halogenoalkyl group, a silyl group, a siloxy group, an acyloxy group and a carbonyl group having one monovalent group, the same groups as specifically described in the description of $R^{13}$ and $R^{14}$ in the aforementioned scheme (9) can be recited.

When $R^{28}$ and $R^{29}$, $R^{28}$ and $R^{30}$, and $R^{28}$ and $R^{29}$ and $R^{30}$ in the scheme (16) bind to each other, the reaction is intermolecular reaction, and the reaction product is a cyclic compound such as cyclic amine. When $R^{29}$ and $R^{30}$ bind to each other, alcohols form cyclic compounds such as cyclic alcohol. When $R^{29}$ and $R^{30}$ in the scheme (17) bind to each other, alcohols form cyclic compounds such as cyclic alcohol. When $R^{32}$ and $R^{31}$ bind to each other, amines form cyclic amine. Also, $R^{32}$ and $R^{30}$ and/or $R^{29}$, $R^{32}$ and $R^{31}$ and $R^{30}$ and/or $R^{29}$, and $R^{31}$ and $R^{30}$ and/or $R^{29}$ bind to each other, the reaction is intermolecular reaction, and the reaction product is a cyclic compound such as cyclic amine.

In the schemes (16) and (17), when $R^{28}$ to $R^{32}$ each independently represent an alkenyl group or an alkynyl group, or $R^{28}$ to $R^{32}$ each independently have an alkenyl group, an alkynyl group, an acyloxy group and/or a carbonyl group having one monovalent group as a substituent, these groups may be reduced in the reaction process.

In the schemes (16) and (17), when $R^{28}$ to $R^{32}$ each independently have an aralkyloxy group as a substituent, the aralkyloxy group may be reduced in the reaction process.

In the schemes (16) and (17), when $R^{28}$ to $R^{32}$ each independently have a hydroxyl group as a substituent, the hydroxyl group may be oxidized in the reaction process.

While the dehydration condensation between alcohols and amines of the present invention can be preferably conducted in the absence or in the presence of solvent (s), it is desired to use solvent (s). The solvent and the use amount of the solvent can be the same as the solvent and the use amount of the solvent as specifically described in the dehydrogenation of alcohols, hemiacetals and hemiaminals.

In the dehydration condensation between alcohols and amines of the present invention, additive(s) may be added appropriately. As the additive, the same additive as the additive specifically described in the hydrogenation of ketones can be recited.

The present reaction is desirably conducted in an inert gas atmosphere, hydrogen gas atmosphere, carbon monoxide gas atmosphere or air atmosphere. As an inert gas, concretely, argon gas, nitrogen gas and the like can be recited. These gases and atmospheric air may be used individually or used as a mixed gas.

In the present reaction, since the dehydrogenation and the hydrogenation can be carried out in the same system, a hydrogen donor is not necessarily required, however, a hydrogen donor such as hydrogen gas, formic acid or the like may be used. The pressure at the time of using hydrogen gas as a hydrogen donor is normally between atmospheric pressure and 10 MPa, preferably between atmospheric pressure and 5 MPa, more preferably between atmospheric pressure and 2 MPa. The atmospheric pressure means the pressure under a hydrogen gas atmosphere where pressurization of hydrogen gas is not required.

The reaction temperature is appropriately selected normally in the range of −50° C. to 200° C., preferably in the range of 0° C. to 180° C., more preferably in the range of 20° C. to 150° C.

While the reaction time naturally varies depending on the solvent, the reaction temperature and other conditions, it is appropriately selected normally in the range of 1 minute to 72 hours, preferably in the range of 1 minute to 24 hours, more preferably in the range of 5 minutes to 12 hours.

The product may be subject to a post treatment, isolation and purification as needed. As a method of a post treatment, for example, concentration, washing, extraction, backward extraction, and crystallization by addition of a poor solvent can be recited, and these may be conducted solely or in combination. As a method for isolation and purification, for example, drying up of a reaction solution, various kinds of chromatography, distillation, recrystallization and washing of crystals with a poor solvent can be recited, and these may be conducted solely or in combination.

Any of the aforementioned reactions using a ruthenium complex represented by the general formula (1) can be conducted while a complex is formed (in situ method). For example, a ruthenium complex represented by the aforementioned general formula (7), NHC (NHC represents an N-heterocyclic carbene derived from a nitrogen-containing heterocyclic ring, or an optically active form thereof.) or an NHC equivalent, a substrate, solvent (s) and additive (s) as necessary are hermetically sealed in the same vessel, and hydrogenation of ketones, aldehydes, esters and amides can be conducted in the presence of a hydrogen donor. Regarding the solvent, the use amount of the solvent, the hydrogen donor, the additive, the reaction temperature, the pressure in the case of using hydrogen gas, the post treatment, the isolation and the purification, the same conditions as the solvent, the use amount of the solvent, the hydrogen donor, the additive, the reaction temperature, the pressure in the case of using hydrogen gas, the post treatment, the isolation and the purification specifically described in the hydrogenation of ketones in the scheme (9) can be recited.

In the same manner, it is possible to conduct dehydrogenation of alcohols, hemiacetals and hemiaminals by hermetically sealing a ruthenium complex represented by the general formula (7), NHC (NHC represents an N-heterocyclic carbene derived from a nitrogen-containing heterocyclic ring, or an optically active form thereof.) or an NHC equivalent, a substrate, solvent(s) and additive(s) as necessary in the same vessel. Regarding the solvent, the use amount of the solvent, the additive, the reaction temperature, the post treatment, the isolation and the purification in the present reaction, the same conditions as the solvent, the use amount of the solvent, the additive, the reaction temperature, the pressure when hydrogen gas is used, the post treatment, the isolation and the purification as specifically described in dehydrogenation of alcohols, hemiacetals and hemiaminals in the schemes (13), (14) and (15) can be recited.

Also, it is possible to conduct N-alkylation reaction via condensation between alcohols and amines by hermetically sealing a ruthenium complex represented by the general formula (7), NHC (NHC represents an N-heterocyclic carbene derived from a nitrogen-containing heterocyclic ring, or an optically active form thereof.) or an NHC equivalent, a substrate (amines and alcohols), solvent(s), a hydrogen donor as necessary, and additive(s) as necessary in the same vessel. Regarding the solvent, the use amount of the solvent, the hydrogen donor, the additive, the reaction temperature, the pressure when hydrogen gas is used, the post treatment, the isolation and the purification in the present reaction, the same conditions as the solvent, the use amount of the solvent, the hydrogen donor, the additive, the reaction temperature, the pressure when hydrogen gas is used, the post treatment, the isolation and the purification as specifically described in N-alkylation reaction in the schemes (16) and (17) can be recited.

Also it is possible to enclose a ruthenium complex represented by the aforementioned general formula (8), PNP (PNP represents a tridentate ligand represented by the general formula (2), (3) or (4), or an optically active form thereof.), a substrate, solvent (s) and additive (s) as necessary in the same vessel, and to conduct hydrogenation of ketones, aldehydes, esters and amides in the presence of a hydrogen donor. Regarding the solvent, the use amount of the solvent, the hydrogen donor, the additive, the reaction temperature, the pressure in the case of using hydrogen gas, the post treatment, the isolation and the purification in the present reaction, the same conditions as the solvent, the use amount of the solvent, the hydrogen donor, the additive, the reaction temperature, the pressure in the case of using hydrogen gas, the post treatment, the isolation and the purification specifically described in the hydrogenation of ketones in the scheme (11) can be recited.

In the same manner, it is possible to conduct dehydrogenation of alcohols, hemiacetals and hemiaminals by hermetically sealing a ruthenium complex represented by the general formula (8), PNP (PNP represents a tridentate ligand represented by the general formula (2), (3) or (4), or an optically active form thereof.), a substrate, solvent(s) and additive(s) as necessary in the same vessel. Regarding the solvent, the use amount of the solvent, the additive, the reaction temperature, the post treatment, the isolation and the purification in the present reaction, the same conditions as the solvent, the use amount of the solvent, the additive, the reaction temperature, the pressure when hydrogen gas is used, the post treatment, the isolation and the purification as specifically described in dehydrogenation of alcohols, hemiacetals and hemiaminals in the schemes (13), (14) and (15) can be recited.

Also, it is possible to conduct N-alkylation reaction via condensation between alcohols and amines by hermetically sealing a ruthenium complex represented by the general formula (8), PNP (PNP represents a tridentate ligand represented by the general formula (2), (3) or (4), or an optically active form thereof.), a substrate (amines and alcohols), solvent(s), a hydrogen donor as necessary, and additive(s) as necessary in the same vessel. Regarding the solvent, the use amount of the solvent, the hydrogen donor, the additive, the reaction temperature, the pressure when hydrogen gas is used, the post treatment, the isolation and the purification in the present reaction, the same conditions as the solvent, the use amount of the solvent, the hydrogen donor, the additive, the reaction temperature, the pressure when hydrogen gas is used, the post treatment, the isolation and the purification as specifically described in N-alkylation reaction in the schemes (16) and (17) can be recited.

EXAMPLES

Hereinafter, the present invention will be specifically described by way of examples, however, it is to be noted that the present invention is not limited by any means by these examples.

Any structural formula in Examples does not consider facial/meridional isomers of a metal complex having a tridentate ligand, geometrical isomers such as cis/trans isomers of a metal complex having a plurality of monodentate ligands and so on.

GC yield was determined by gas chromatography (hereinafter, abbreviated as GC). The used apparatus is as follows. Proton nuclear magnetic resonance spectrum (hereinafter, abbreviated as $^1$H NMR.);
MERCURY 300-C/H (Resonance frequency: 300 MHz, available from VARIAN) or 400MR/DD2 (Resonance frequency: 400 MHz, available from Agilent)
Phosphorus 31 nuclear magnetic resonance spectrum (hereinafter, abbreviated as $^{31}$P NMR.);
MERCURY 300-C/H (Resonance frequency: 121 MHz, available from VARIAN) or 400MR/DD2 (Resonance frequency: 161 MHz, available from Agilent)
Gas chromatography (GC);
GC-4000 (available from GL-SCIENCES)
InertCAP PureWAX (30 m, 0.25 mmID, 0.25 μm df)
Inj. Temp.; 200° C., Det. Temp.; 250° C.
Temp. 50° C. (0 min.) –5° C./min. –150° C. (0 min.) –10° C./min. –250° C. (5 min.)

HRMS;
LCMS-IT-TOF (Ionization: ESI, or APCI, available from Shimadzu) MS;
JMS-T100GCV (Ionization: FD, available from JEOL)

Example 1

Ruthenium complex B was produced in the following scheme.

[Chemical Formula 20]

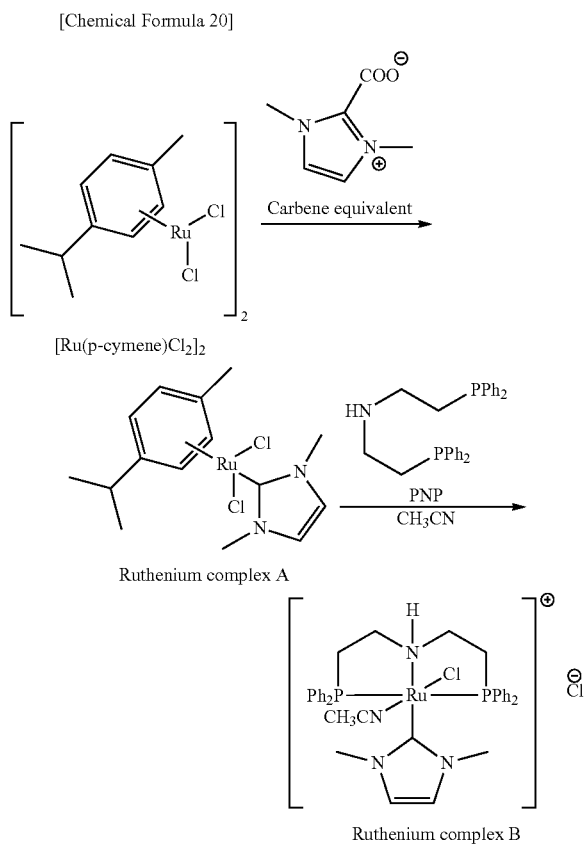

In a 100 mL flask, 981 mg (3.2 mmol/Ru) of [Ru(p-cymene)Cl$_2$]$_2$, and 472 mg (3.37 mmol) of a carbene equivalent were added, and after replacement with nitrogen gas, 50 mL of acetonitrile was added, and heated to reflux for 2 hours. After cooling to ambient temperature, 1.44 g (3.37 mmol) of PNP was added and heated to reflux for another 4 hours. After cooling to ambient temperature, precipitated crystals were separated by filtration and dried in vacuo to obtain target ruthenium complex B as 590.1 mg (0.79 mmol) of pale yellow crystals.

$^1$H NMR (300 MHz, CD$_2$Cl$_2$)
δ=2.71 (s, 3H), 2.90-3.20 (m, 6H), 3.25-3.40 (m, 3H), 3.36 (s, 6H), 6.84 (dd, J=1.8 Hz, 12.0 Hz, 2H), 7.28-7.50 (m, 20H)
$^{31}$P NMR (121 MHz, CD$_2$Cl$_2$): δ=43.8
HRMS (ESI, m/z)
Calculated value: 715.1461 as C$_{35}$H$_{40}$N$_4$P$_2$ClRu ([M−Cl]$^+$),
Measured value: 715.1433

An ORTEP view prepared from the result of X-ray structural analysis of ruthenium complex B is shown as FIG. 1.

Example 2

Ruthenium complex A was produced in the following scheme.

[Chemical Formula 21]

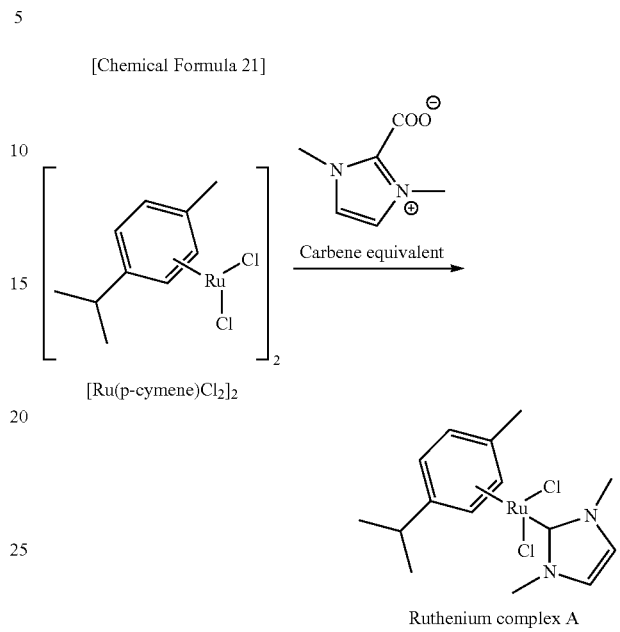

In a 300 mL flask, 3.85 g (12.6 mmol/Ru) of [Ru (p-cymene) Cl$_2$]$_2$, and 1.83 g (13.1 mmol) of a carbene equivalent were added, and after replacement with nitrogen gas, 25 mL of tetrahydrofuran (hereinafter, indicated by THF) was added, and heated to reflux for 4 hours. After cooling to ambient temperature, 15 mL of THF was distilled off in vacuo, and 10 mL of 2-propanol was added, and then stirred at 40° C. for 10 minutes. After cooling to ambient temperature, 5 mL of hexane was added, and stirred with an ice bath for 1 hour. The precipitated crystals were separated by filtration, and then washed with hexane, and dried in vacuo to obtain ruthenium complex A as 4.20 g (10.44 mmol) of orange crystals.

$^1$H NMR (300 MHz, CD$_2$Cl$_2$)
δ=1.24 (d, J=6.9 Hz, 6H), 1.98 (s, 3H), 2.92 (quin, J=6.9 Hz, 1H), 4.00 (s, 6H), 5.06 (d, J=6.0 Hz, 2H), 5.39 (d, J=6.0 Hz, 2H), 7.02 (s, 2H)
HRMS (ESI, m/z)
Calculated value: 367.0510 as C$_{15}$H$_{22}$N$_2$ClRu ([M−Cl]$^+$)
Measured value: 367.0493

Example 3

Ruthenium complex B was produced in the following scheme.

[Chemical Formula 22]

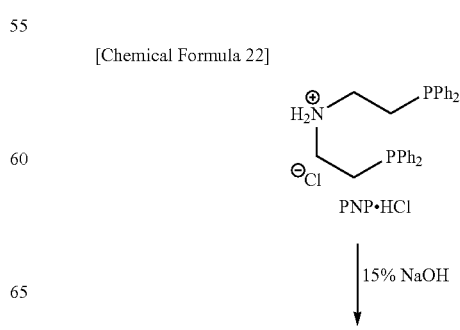

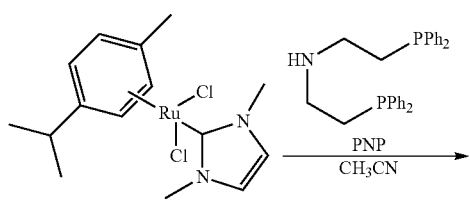

Ruthenium complex A

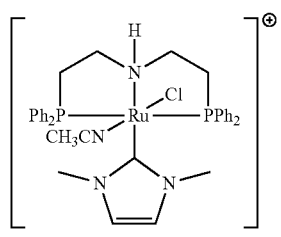

Ruthenium complex B

In a 50 mL flask, 375 mg (0.78 mmol) of PNP.HCl, 10 mL of toluene, and 10 mL of a 15% NaOH aqueous solution were added, and stirred at ambient temperature until the solid disappeared. After separating the reaction solution, the organic layer was washed with distilled water (5 mL×2), and then the organic layer was dried over sodium sulfate, and the solvent was distilled off to obtain PNP.

In a 50 mL flask, 287 mg (0.71 mmol) of ruthenium complex A was added, and after replacement with nitrogen gas, 25 mL of acetonitrile, and a solution of the PNP obtained in the above in acetonitrile (5 mL) were added, and heated to reflux for 2 hours. After cooling to ambient temperature, the precipitated crystals were separated by filtration, and dried in vacuo to obtain target ruthenium complex B as 161.0 mg (0.21 mmol) of pale yellow crystals.

Example 4

Ruthenium complex C was produced in the following scheme.

[Chemical Formula 23]

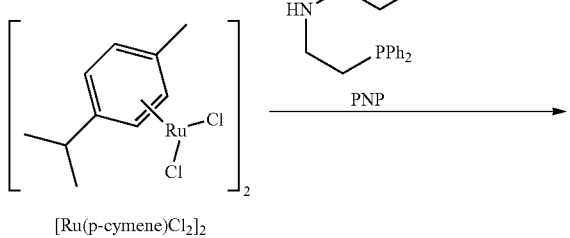

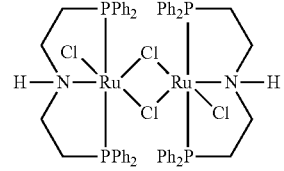

Ruthenium complex C

In a 20 mL side-arm flask, 0.189 g (0.40 mmol) of PNP*HCl, 4 mL of toluene, and 2 mL of a 15% NaOH aqueous solution were added, and stirred at ambient temperature until the solid disappeared. After separating the solution, the organic layer was washed with distilled water (2 mL×2), and then the organic layer was dried over sodium sulfate, and the solvent was distilled off to obtain PNP.

In a hermetical reaction vessel, 109 mg (0.36 mmol/Ru) of [Ru(p-cymene)Cl$_2$]$_2$ was added, and after replacement with nitrogen gas, a solution of the PNP obtained in the above in 2-propanol (3 mL) was added, and reacted at 120° C. for 2 hours, then at 150° C. for 2 hours. After cooling to ambient temperature, the precipitated crystals were separated by filtration, washed with 2-propanol (1 mL), then dried in vacuo, to obtain target ruthenium complex C as 176.1 mg (0.29 mmol/Ru) of orange crystals.

$^1$H NMR (300 MHz, CD$_2$Cl$_2$)

δ=2.05-2.30 (m, 4H), 2.65-2.80 (m, 4H), 2.80-3.00 (m, 4H), 3.30-3.50 (m, 4H), 6.68-6.80 (m, 4H), 6.82-6.92 (m, 8H), 7.00-7.18 (m, 20H), 7.70-7.90 (m, 8H)

$^{31}$P NMR (121 MHz, CD$_2$Cl$_2$): δ=64.3

HRMS (ESI, m/z)

Calculated value: 1191.0698 as C$_{56}$H$_{58}$N$_2$P$_4$Cl$_3$Ru$_2$ ([M−Cl]$^+$)

Measured value: 1191.0701

Example 5

Ruthenium complex D was produced in the following scheme.

[Chemical Formula 24]

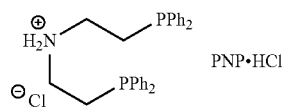

PNP·HCl

↓ 15% NaOH

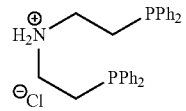

PNP

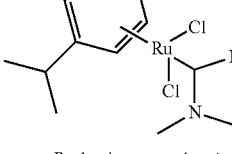

Ruthenium complex A

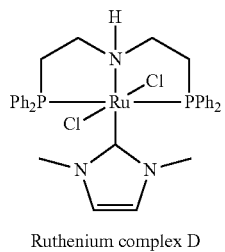

Ruthenium complex D

In a 50 mL flask, 724 mg (1.51 mmol) of PNP.HCl, 10 mL of toluene, and 10 mL of a 15% NaOH aqueous solution were added, and stirred at ambient temperature until the solid disappeared. After separating the reaction solution, the organic layer was washed with distilled water (5 mL×2), and then the organic layer was dried over sodium sulfate, and the solvent was distilled off to obtain PNP. To the obtained PNP, 3 mL of ethanol was added to prepare a PNP solution.

In a 20 mL flask, 609.3 mg (1.51 mmol) of ruthenium complex A was added, and after replacement with nitrogen gas, the obtained PNP solution was added, and reacted at 70° C. for 2 hours. After cooling to ambient temperature, concentration in vacuo was conducted and ethanol was distilled off. To the obtained viscous solution, hexane was added to make a solid precipitate, and after removing the solvent by decantation, concentration in vacuo was conducted. After washing the obtained solid with ethyl acetate and hexane, the solid was dried in vacuo to obtain target ruthenium complex D as 916.8 mg (1.29 mmol) of ocher crystals.

$^1$H NMR (300 MHz, CD$_2$Cl$_2$)

δ=2.50-2.80 (m, 2H), 2.95-3.15 (m, 2H), 3.05 (s, 3H), 3.19 (s, 3H), 3.19-3.50 (m, 4H), 4.20-4.40 (m, 1H), 6.68-6.80 (m, 2H), 7.20-7.60 (m, 20H)

$^{31}$P NMR (121 MHz, CD$_2$Cl$_2$): δ=42.5

HRMS (ESI, m/z)

Calculated value: 674.1195 as C$_{33}$H$_{37}$N$_3$P$_2$ClRu ([M−Cl]$^+$)

Measured value: 674.1190

Example 6

Ruthenium complex E was produced in the following scheme.

[Chemical Formula 25]

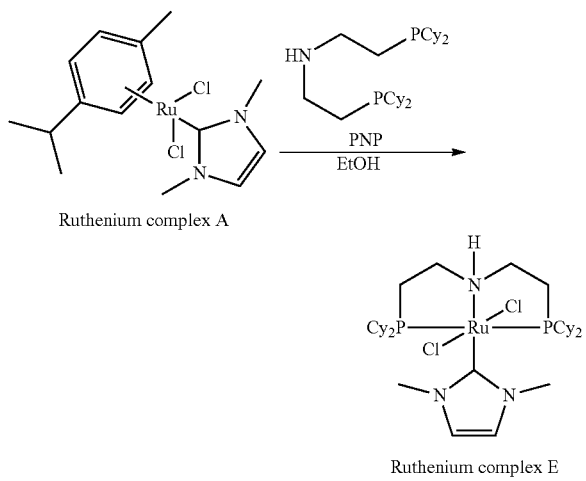

Ruthenium complex E

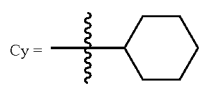

In a 20 mL side-arm flask, 93.1 mg (0.20 mmol) of PNP, and 80.5 mg (0.20 mmol) of ruthenium complex A were added, and after replacement with nitrogen gas, 2.0 mL of ethanol was added. After stirring at 40° C. for 2 hours, the reaction mixture was cooled to ambient temperature, and about 1.0 mL of ethanol was distilled off in vacuo. After separating the precipitated solid by filtration, the obtained solid was washed with hexane (3 mL) and dried in vacuo to obtain target ruthenium complex E as 41.0 mg (0.056 mmol) of pink crystals.

$^1$H NMR (400 MHz, CD$_2$Cl$_2$)

δ=1.00-3.10 (m, 52H), 3.53 (s, 3H), 3.67 (s, 3H), 3.90-4.20 (bs, 1H), 6.70-6.80 (m, 2H)

$^{31}$P NMR (161 MHz, CD$_2$Cl$_2$): δ=43.1

HRMS (ESI, m/z)

Calculated value: 698.3073 as C$_{33}$H$_{61}$N$_3$P$_2$ClRu ([M−Cl]$^+$)

Measured value: 698.3047

Example 7

Ruthenium complex F was produced in the following scheme.

[Chemical Formula 26]

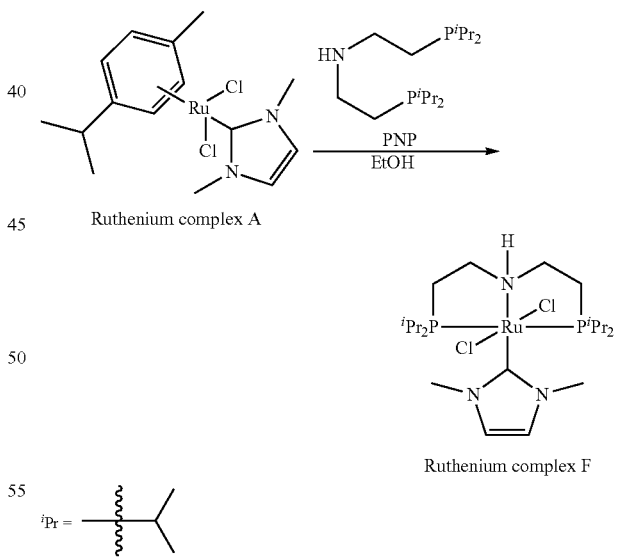

In a 20 mL side-arm flask, 320.2 mg (1.05 mmol) of PNP was added, and after replacement with nitrogen gas, 402.32 mg (1.00 mmol) of ruthenium complex A and 10 mL of ethanol were added. After stirring at 40° C. for 3 hours, the reaction mixture was cooled to ambient temperature, and about 7.0 mL of ethanol was distilled off in vacuo. After separating the precipitated solid by filtration, the solid was washed with hexane (3 mL), and dried in vacuo to obtain target ruthenium complex F as 111.1 mg (0.19 mmol) of pink crystals.

$^1$H NMR (400 MHz, CD$_2$Cl$_2$)

δ=1.00-1.40 (m, 24H), 1.68-1.82 (m, 2H), 2.34-2.48 (m, 2H), 2.70-3.10 (m, 8H), 3.40 (s, 3H), 3.74 (s, 3H), 4.00-4.20 (m, 1H), 6.75-6.80 (m, 2H)

$^{31}$P NMR (161 MHz, CD$_2$Cl$_2$): δ=48.9

HRMS (ESI, m/z)

Calculated value: 538.1818 as C$_{21}$H$_{45}$N$_3$P$_2$ClRu ([M−Cl]$^+$)

Measured value: 538.1807

Example 8

Ruthenium complex G was produced in the following scheme.

[Chemical Formula 27]

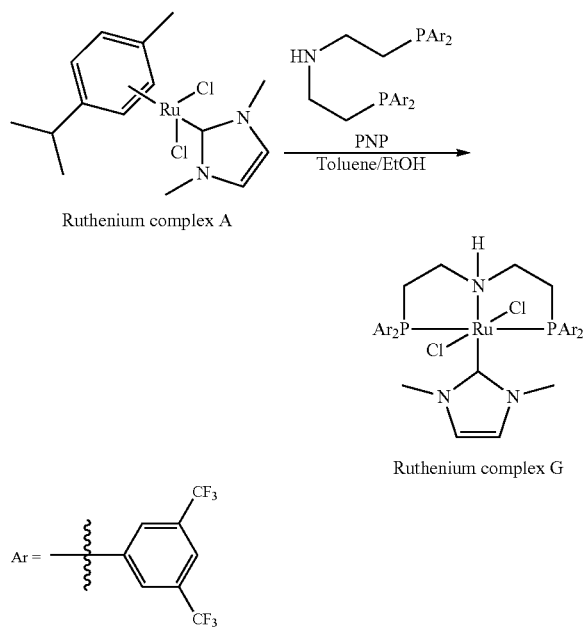

Ruthenium complex A

Ruthenium complex G

Ar = 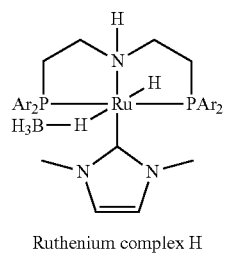

In a 20 mL side-arm flask, 1.71 g (1.74 mmol) of PNP was added, and after replacement with nitrogen gas, 15.5 mL of toluene, 1.7 mL of ethanol, and 700 mg (1.74 mmol) of ruthenium complex A were added. After stirring at 100° C. for 2 hours, the reaction mixture was cooled to ambient temperature, and the solvent was distilled off in vacuo. The precipitated solid was washed with hexane (3 mL), and dried in vacuo to obtain target ruthenium complex G as 2.01 g (1.60 mmol) of ocher crystals.

$^1$H NMR (400 MHz, CD$_2$Cl$_2$)

δ=2.70-2.86 (m, 2H), 2.99 (s, 3H), 3.11 (s, 3H), 3.12-3.28 (m, 2H), 3.30-3.48 (m, 4H), 4.27-4.45 (m, 1H), 6.82-6.90 (m, 2H), 7.70-7.80 (m, 4H), 7.82-7.88 (m, 4H), 7.90-7.98 (m, 4H)

$^{31}$P NMR (161 MHz, CD$_2$Cl$_2$): δ=48.9

HRMS (APCI, m/z)

Calculated value: 1252.9874 as C$_{41}$H$_{29}$N$_3$F$_{24}$P$_2$Cl$_2$Ru ([M]$^+$)

Measured value: 1252.9865

Example 9

Ruthenium complex H was produced in the following scheme.

[Chemical Formula 28]

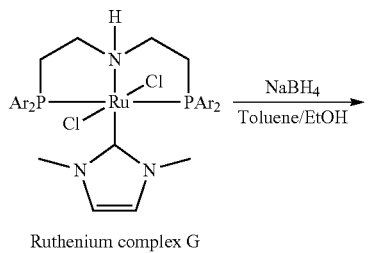

Ruthenium complex G

Ruthenium complex H

Ar = 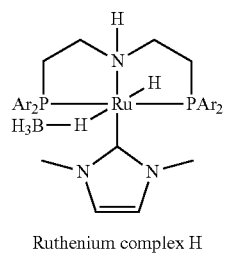

In a 20 mL side-arm flask, 166 mg (0.132 mmol) of ruthenium complex G, and 50 mg (1.32 mmol) of sodium borohydride (NaBH$_4$) were added, and after replacement with nitrogen gas, toluene (1.7 mL) and ethanol (1.7 mL) were added. After stirring at 65° C. for 15 minutes, the reaction mixture was cooled to ambient temperature, and the solvent was distilled off in vacuo. After adding 2 mL of methylene chloride, and separating an insoluble matter by filtration, the filtrate was distilled off in vacuo again, and the obtained solid was dried in vacuo to obtain about 50 mg of a complex. The obtained compound is a mixture of ruthenium complex G and target ruthenium complex H, and as a result of $^1$H NMR analysis, a peak derived from hydride on ruthenium in ruthenium complex H was observed in the range of −15.00 to −16.00 ppm, and a peak derived from H—BH$_3$ on ruthenium in ruthenium complex H was observed in the range of −1.40 to −3.20 ppm. As a result of $^{31}$P NMR analysis, a peak derived from ruthenium complex H was observed at 64.3 ppm.

HRMS (ESI, m/z)

Calculated value: 1184.0581 as C$_{41}$H$_{30}$N$_3$F$_{24}$P$_2$Ru ([M−BH$_4$]$^+$)

Measured value: 1184.0616

MS (FD, m/z)

Calculated value: 1199 as C$_{41}$H$_{34}$N$_3$BF$_{24}$P$_2$Ru ([M]$^+$)

Measured value: 1199

Example 10

Ruthenium complex I was produced in the following scheme.

[Chemical Formula 29]

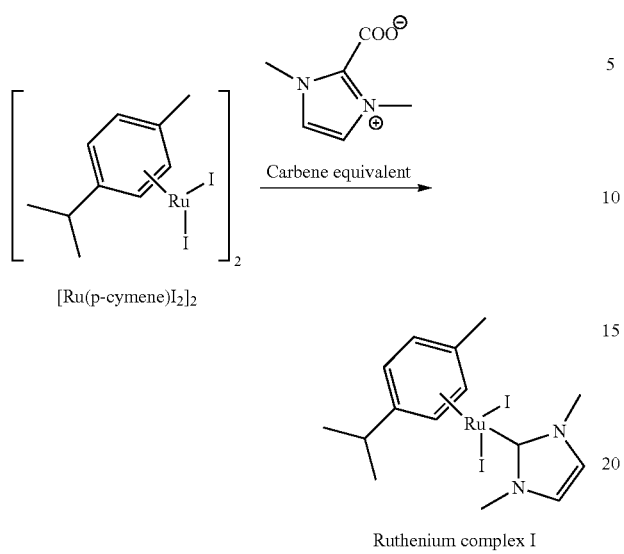

Ruthenium complex I

In a 20 mL side-arm flask, 500.7 mg (1.02 mmol/Ru) of Ru (p-cymene)I$_2$]$_2$, and 152 mg (1.08 mmol) of a carbene equivalent were added, and after replacement with nitrogen gas, 10 mL of THF was added, and heated to reflux for 3.5 hours. After cooling to ambient temperature, the solvent was distilled off in vacuo, and 5 mL of 2-propanol was added. The precipitated solid was separated by filtration, and washed with 2-propanol and hexane, and then dried in vacuo to obtain 414.1 mg (0.71 mmol) of target ruthenium complex G.

$^1$H NMR (400 MHz, CD$_2$Cl$_2$)

δ=1.08-1.30 (m, 6H), 1.95 (s, 3H), 3.05-3.22 (m, 1H), 4.05 (s, 6H), 5.10-5.20 (m, 2H), 5.50-5.70 (m, 2H), 7.00-7.20 (m, 2H)

HRMS (ESI, m/z)

Calculated value: 458.9870 as C$_{15}$H$_{22}$N$_2$IRu ([M–I]$^+$)

Measured value: 458.9852

Example 11

Hydrogenation of Methyl Benzoate

In a 100 mL stainless autoclave, 1.9 mg (0.0025 mmol/Ru) of ruthenium complex B produced in Example 1 was added, and after replacement with nitrogen gas, 0.25 mL (0.25 mmol) of a 1 M KO$^t$Bu (potassium tert-butoxide) solution in THF, 2 mL of toluene, and 0.31 mL (2.5 mmol) of a substrate were added, and then stirred at 1 MPa of hydrogen pressure at 80° C. for 6 hours. After cooling, the reactant was analyzed by GC, and benzyl alcohol was obtained with a GC yield of 71%.

Examples 12 to 17

The results when hydrogenation of methyl benzoate was conducted in the same manner as in Example 11 are shown in Table 1.

TABLE 1

| Example | Substrate (mmol) | Ru complex (mmol/Ru) | KO$^t$Bu (mmol) | Solvent (mL) | Hydrogen pressure (MPa) | Temperature (° C.) | Time (hr) | GC yield (%) |
|---|---|---|---|---|---|---|---|---|
| 12 | 2.5 | D (0.0027) | 0.25 | Tol (2.0) | 1.0 | 80 | 6 | >99 |
| 13 | 1.0 | D (0.0100) | 0.10 | THF (1.8) | balloon | 50 | 6 | 88 |
| 14 | 1.0 | D (0.0200) | 0.10 | THF (1.8) | balloon | 50 | 6 | >99 |
| 15 | 2.5 | E (0.0025) | 0.25 | Hex (5.0) | 1.0 | 80 | 6 | 60 |
| 16 | 2.5 | F (0.0025) | 0.25 | Hex (5.0) | 1.0 | 80 | 6 | 54 |
| 17 | 2.5 | G (0.0025) | 0.25 | THF (2.0) | 1.0 | 80 | 6 | 78 |

Solvent: Tol = toluene, THF = tetrahydrofuran, Hex = hexane
In Examples 13 and 14, a 50 mL glass Schlenk tube was used for reaction.

Example 18

Hydrogenation of Methyl Benzoate

To a 100 mL stainless autoclave, 1.5 mg (0.0024 mmol/Ru) of ruthenium complex C produced in Example 4, and 1.0 mg (0.0074 mmol) of a carbene equivalent (NHC-a) were added, and after replacement with nitrogen gas, 0.25 mL (0.25 mmol) of 1 M KO$^t$Bu (solution in THF), 2 mL of toluene, 0.31 mL (2.5 mmol) of a substrate were added, and then stirred at 1 MPa of hydrogen pressure at 80° C. for 6 hours. After cooling, the reactant was analyzed by GC, and benzyl alcohol was obtained with a GC yield of 93%.

Examples 19 to 29

The results when hydrogenation of methyl benzoate was conducted in the same manner as in Example 18 are shown in Table 2.

TABLE 2

| Example | Substrate (mmol) | Ru complex C (mmol/Ru) | Carbene equivalent (mmol) | KO$^t$Bu (mmol) | Solvent (mL) | GC yield (%) |
|---|---|---|---|---|---|---|
| 19 | 2.5 | 0.0024 | NHC-b (0.0060) | 0.25 | Tol (2.0) | >99 |
| 20 | 2.5 | 0.0024 | NHC-c (0.0071) | 0.25 | Tol (2.0) | 86 |
| 21 | 6.0 | 0.0060 | NHC-d (0.0059) | 0.60 | Tol (4.8) | 94 |

TABLE 2-continued

| Example | Substrate (mmol) | Ru complex C (mmol/Ru) | Carbene equivalent (mmol) | KO$^t$Bu (mmol) | Solvent (mL) | GC yield (%) |
|---|---|---|---|---|---|---|
| 22 | 2.5 | 0.0024 | NHC-e (0.0026) | 0.25 | Tol (2.0) | 84 |
| 23 | 2.5 | 0.0024 | NHC-f (0.0025) | 0.25 | Tol (2.0) | 90 |
| 24 | 2.5 | 0.0024 | NHC-g (0.0050) | 0.25 | Tol (2.0) | 60 |
| 25 | 2.5 | 0.0024 | NHC-h (0.0049) | 0.25 | Tol (2.0) | 13 |
| 26 | 2.5 | 0.0024 | NHC-i (0.0025) | 0.25 | Tol (2.0) | 13 |
| 27 | 6.0 | 0.0060 | NHC-j (0.0058) | 0.60 | THF (4.8) | 79 |
| 28 | 6.0 | 0.0060 | NHC-k (0.0062) | 0.60 | THF (4.8) | 31 |
| 29 | 6.0 | 0.0060 | NHC-l (0.0062) | 0.60 | THF (4.8) | >99 |

100 mL autoclave, Hydrogen pressure = 1.0 MPa, Reaction temperature = 80° C., Reaction time = 6 hours In Table 2, Tol represents toluene, and THF represents tetrahydrofuran.

Carbene equivalents indicated by NHC-alphabet in Example 18 and Table 2 are respectively those shown below. Also in Examples shown below, the same sign is used for a carbene equivalent.

[Chemical Formula 30]

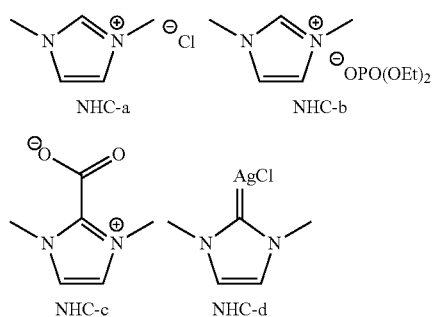

NHC-a  NHC-b

NHC-c  NHC-d

NHC-e

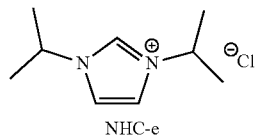

NHC-f

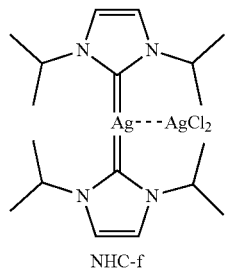

NHC-g

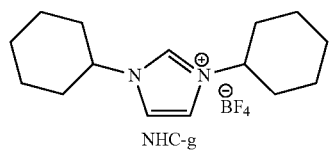

NHC-h

-continued

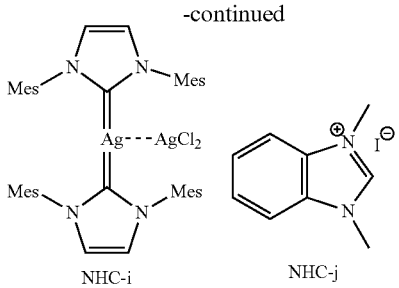

NHC-i  NHC-j (Mes = 2,4,6-trimethylphenyl)

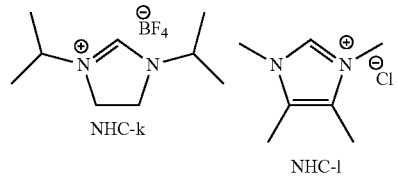

NHC-k  NHC-l

Example 30

Hydrogenation of Methyl Benzoate

In a 100 mL stainless autoclave, 1.0 mg (0.0025 mmol/Ru) of ruthenium complex A produced in Example 2, and 1.2 mg (0.0025 mmol) of PNP.HCl were added, and after replacement with nitrogen gas, 0.25 mL (0.25 mmol) of 1 M KO$^t$Bu (solution in THF), 2 mL of toluene, and 0.31 mL (2.5 mmol) of a substrate were added, and then stirred at 1 MPa of hydrogen pressure at 40° C. for 6 hours. After cooling, the reactant was analyzed by GC, and benzyl alcohol was obtained with a GC yield of 66%.

Example 31

Hydrogenation of Methyl Benzoate

In a 100 mL stainless autoclave, 1.5 mg (0.0025 mmol/Ru) of ruthenium complex I produced in Example 10, and 1.2 mg (0.0025 mmol) of PNP.HCl were added, and after replacement with nitrogen gas, 0.25 mL (0.25 mmol) of 1 M KO$^t$Bu (solution in THF), 2 mL of toluene, and 0.31 mL (2.5 mmol) of methyl benzoate were added, and then stirred at 1 MPa of hydrogen pressure at 80° C. for 6 hours. After cooling, the reactant was analyzed by GC, and benzyl alcohol was obtained with a GC yield of 90%.

Example 32

Hydrogenation of Methyl Lactate

In a 100 mL stainless autoclave, 3.7 mg (0.0060 mmol/Ru) of ruthenium complex C produced in Example 4, and 1.3 mg (0.0059 mmol) of a carbene equivalent (NHC-d) were added, and after replacement with nitrogen gas, 0.6 mL (0.6 mmol) of 1 M KO$^t$Bu (solution in THF), 4.8 mL of toluene, and 0.57 mL (6.0 mmol) of a substrate were added, and then stirred at 1 MPa of hydrogen pressure at 80° C. for 6 hours. After cooling, the reactant was analyzed by GC, and 1,2-propanediol was obtained with a GC yield of 78%.

Example 33

Hydrogenation of Methyl Lactate

The same operation was conducted as in Example 32 except that 1.13 M NaOMe (sodium methoxide) (solution in methanol) was used in place of 1M KO$^t$Bu (solution in THF), and methanol was used in place of toluene in Example 32, and 1,2-propanediol was obtained with a GC yield of 80%.

Example 34

Hydrogenation of Methyl Lactate

In a 50 mL glass Schlenk tube, 7.1 mg (0.0100 mmol/Ru) of ruthenium complex D produced in Example 5 was added, and after replacement with nitrogen gas, 0.50 mL (0.50 mmol) of 1 M KO$^t$Bu (solution in THF), 1.4 mL of THF, 0.096 mL (1.0 mmol) of a substrate were added, and then a balloon containing hydrogen gas was attached to the Schlenk tube to conduct replacement with hydrogen gas, and stirred at 50° C. for 6 hours. After cooling, the reactant was analyzed by GC, and propanediol was obtained with a GC yield of 94%.

Example 35

Hydrogenation of Methyl Lactate

In a 50 mL glass Schlenk tube, 14.2 mg (0.0200 mmol/Ru) of ruthenium complex D produced in Example 5 was added, and after replacement with nitrogen, 0.20 mL (0.20 mmol) of 1 M KO$^t$Bu (solution in THF), 3.8 mL of THF, and 0.096 mL (1.0 mmol) of a substrate were added, and then a balloon containing hydrogen gas was attached to the Schlenk tube to conduct replacement with hydrogen gas, and stirred at 50° C. for 6 hours. After cooling, the reactant was analyzed by GC, and propanediol was obtained with a GC yield of 91%.

Example 36

Hydrogenation of Methyl Picolinate

In a 100 mL stainless autoclave, 3.7 mg (0.0060 mmol/Ru) of ruthenium complex C produced in Example 4, and 1.3 mg (0.0059 mmol) of a carbene equivalent (NHC-d) were added, and after replacement with nitrogen gas, 0.6 mL (0.6 mmol) of 1 M KO$^t$Bu (solution in THF), 4.8 mL of toluene, and 0.72 mL (6.0 mmol) of a substrate were added, and then stirred at 1 MPa of hydrogen pressure at 80° C. for 6 hours. After cooling, the reactant was analyzed by GC, and 2-pyridinemethanol was obtained with a GC yield of 94%.

Example 37

Hydrogenation of Methyl Picolinate

In a 50 mL glass Schlenk tube, 7.1 mg (0.0100 mmol/Ru) of ruthenium complex D produced in Example 5 was added, and after replacement with nitrogen gas, 0.10 mL (0.10 mmol) of 1 M KO$^t$Bu (solution in THF), 1.8 mL of THF, and 0.126 mL (1.0 mmol) of a substrate were added, and then a balloon containing hydrogen gas was attached to the Schlenk tube to conduct replacement with hydrogen gas, and stirred at 45° C. for 6 hours. After cooling, the reactant was analyzed by GC, and 2-pyridinemethanol was obtained with a GC yield of 79%.

Example 38

Hydrogenation of Methyl Picolinate

In a 50 mL glass Schlenk tube, 14.2 mg (0.0200 mmol/Ru) of ruthenium complex D produced in Example 5 was added, and after replacement with nitrogen gas, 0.10 mL (0.10 mmol) of 1 M KO$^t$Bu (solution in THF), 3.8 mL of THF, and 137 mg (1.0 mmol) of a substrate were added, and then a balloon containing hydrogen gas was attached to the Schlenk tube to conduct replacement with hydrogen gas, and stirred at 50° C. for 6 hours. After cooling, the reactant was analyzed by GC, and 2-pyridinemethanol was obtained with a GC yield of 99%.

Example 39

Hydrogenation of Methyl Nicotinate

In a 50 mL glass Schlenk tube, 7.1 mg (0.0100 mmol/Ru) of ruthenium complex D produced in Example 5 was added, and after replacement with nitrogen gas, 0.10 mL (0.10 mmol) of 1 M KO$^t$Bu (solution in THF), 1.8 mL of THF, and 137 mg (1.0 mmol) of a substrate were added, and then a balloon containing hydrogen gas was attached to the Schlenk tube to conduct replacement with hydrogen gas, and stirred at 50° C. for 6 hours. After cooling, the reactant was analyzed by GC, and 3-pyridinemethanol was obtained with a GC yield of 88%.

Example 40

Hydrogenation of Methyl Nicotinate

In a 50 mL glass Schlenk tube, 14.2 mg (0.0200 mmol/Ru) of ruthenium complex D produced in Example 5 was added, and after replacement with nitrogen gas, 0.10 mL (0.10 mmol) of 1 M KO$^t$Bu (solution in THF), 1.8 mL of THF, and 137 mg (1.0 mmol) of a substrate were added, and then a balloon containing hydrogen gas was attached to the Schlenk tube to conduct replacement with hydrogen gas, and stirred at 50° C. for 6 hours. After cooling, the reactant was analyzed by GC, and 3-pyridinemethanol was obtained with a GC yield of 99%.

Example 41

Hydrogenation of γ-Butyrolactone

In a 100 mL stainless autoclave, 1.9 mg (0.0027 mmol/Ru) of ruthenium complex D produced in Example 5 was added, and after replacement with nitrogen gas, 0.25 mL (0.25 mmol) of 1 M KO$^t$Bu (solution in THF), 2 mL of toluene, and 0.19 mL (2.5 mmol) of a substrate were added, and then stirred at 1 MPa of hydrogen pressure at 80° C. for 6 hours. After cooling, the reactant was analyzed by GC, and 1-phenylethanol was obtained with a GC yield of >99%.

Example 42

Hydrogenation of γ-Butyrolactone

In a 100 mL stainless autoclave, 3.7 mg (0.0060 mmol/Ru) of ruthenium complex C produced in Example 4, and 1.3 mg (0.0059 mmol) of a carbene equivalent (NHC-d) were added, and after replacement with nitrogen gas, 0.6 mL (0.6 mmol) of 1 M KO$^t$Bu (solution in THF), 4.8 mL of toluene, and 0.46 mL (6.0 mmol) of a substrate were added, and then stirred at 1 MPa of hydrogen pressure at 80° C. for 6 hours. After cooling, the reactant was analyzed by GC, and 1,4-butanediol was obtained with a GC yield of >99%.

Example 43

Hydrogenation of γ-Butyrolactone

In a 50 mL glass Schlenk tube, 14.2 mg (0.0200 mmol/Ru) of ruthenium complex D produced in Example 5 was added, and after replacement with nitrogen gas, 0.20 mL (0.20 mmol) of 1 M KO$^t$Bu (solution in THF), 3.8 mL of THF, and 0.076 mL (1.0 mmol) of a substrate were added, and then a balloon containing hydrogen gas was attached to the Schlenk tube to conduct replacement with hydrogen gas, and stirred at 50° C. for 6 hours. After cooling, the reactant was analyzed by GC, and propanediol was obtained with a GC yield of 81%.

Example 44

Hydrogenation of Acetophenone

In a 100 mL stainless autoclave, 1.9 mg (0.0027 mmol/Ru) of ruthenium complex D produced in Example 5 was added, and after replacement with nitrogen gas, 0.25 mL (0.25 mmol) of 1 M KO$^t$Bu (solution in THF), 2 mL of toluene, and 0.29 mL (2.5 mmol) of a substrate were added, and then stirred at 1 MPa of hydrogen pressure at 80° C. for 6 hours. After cooling, the reactant was analyzed by GC, and 1-phenylethanol was obtained with a GC yield of >99%.

Example 45

Hydrogenation of Acetophenone

In a 100 mL stainless autoclave, 3.7 mg (0.0060 mmol/Ru) of ruthenium complex C produced in Example 4, and 1.3 mg (0.0059 mmol) of a carbene equivalent (NHC-d) were added, and after replacement with nitrogen gas, 0.6 mL (0.6 mmol) of 1 M KO$^t$Bu (solution in THF), 4.8 mL of toluene, and 0.7 mL (6.0 mmol) of a substrate were added, and then stirred at 1 MPa of hydrogen pressure at 80° C. for 6 hours. After cooling, the reactant was analyzed by GC, and 1-phenylethanol was obtained with a GC yield of >99%.

Example 46

Hydrogenation of 2,2,6-trimethylcyclohexane carbaldehyde

In a 100 mL stainless autoclave, 1.4 mg (0.0020 mmol/Ru) of ruthenium complex D produced in Example 5 was added, and after replacement with nitrogen gas, 0.20 mL (0.20 mmol) of 1 M KO$^t$Bu (solution in THF), 3.5 mL of THF, and 0.31 g (2.0 mmol) of a substrate were added, and then stirred at 1 MPa of hydrogen pressure at 80° C. for 6 hours. After cooling, the reactant was analyzed by GC, and (2,2,6-trimethylcyclohexyl)methanol was obtained with a GC yield of >99%.

Example 47

Hydrogenation of N,N-dimethylbenzamide

In a 100 mL stainless autoclave, 4.4 mg (0.0062 mmol/Ru) of ruthenium complex D produced in Example 5 was added, and after replacement with nitrogen gas, 0.12 mL (0.12 mmol) of 1 M KO$^t$Bu (solution in THF), 1 mL of toluene, and 180 mg (1.2 mmol) of a substrate were added, and then stirred at 3 MPa of a hydrogen pressure at 100° C. for 6 hours. After cooling, the reactant was analyzed by GC, and benzyl alcohol was obtained with a GC yield of 93%.

Example 48

Hydrogenation of N,N-dimethylbenzamide

In a 100 mL stainless autoclave, 3.7 mg (0.0060 mmol/Ru) of ruthenium complex C produced in Example 4, and 1.3 mg (0.0059 mmol) of a carbene equivalent (NHC-d) were added, and after replacement with nitrogen gas, 0.12 mL (0.12 mmol) of 1 M KO$^t$Bu (solution in THF), 1 mL of toluene, and 180 mg (1.2 mmol) of a substrate were added, and then stirred at 3 MPa of hydrogen pressure at 100° C. for 6 hours. After cooling, the reactant was analyzed by GC, and benzyl alcohol was obtained with a GC yield of 86%.

Example 49

Oxidation of 1-phenylethanol

In a hermetical reaction vessel, 1.9 mg (0.0027 mmol/Ru) of ruthenium complex D produced in Example 5 was added, and after replacement with nitrogen gas, 0.25 mL (0.25 mmol) of 1 M KO$^t$Bu (solution in THF), 2 mL of toluene, and 0.30 mL (2.5 mmol) of a substrate were added, and then stirred at 120° C. for 7 hours. After cooling, the reactant was analyzed by GC, and acetophenone was obtained with a GC yield of 31%.

Example 50

Oxidation of 1-phenylethanol

In a hermetical reaction vessel, 3.7 mg (0.0060 mmol/Ru) of ruthenium complex C produced in Example 4, and 1.3 mg (0.0059 mmol) of a carbene equivalent (NHC-d) were added, and after replacement with nitrogen gas, 0.6 mL (0.6 mmol) of 1 M KO$^t$Bu (solution in THF), 4.8 mL of toluene, and 0.72 mL (6.0 mmol) of a substrate were added, and stirred at 120° C. for 5 hours. After cooling, the reactant was analyzed by GC, and acetophenone was obtained with a GC yield of 29%.

Example 51

Benzylation of Aniline Using Benzyl Alcohol as Carbon Source

In a hermetical reaction vessel, 15.3 mg (0.025 mmol/Ru) of ruthenium complex C produced in Example 4, and 94 mg (0.50 mmol) of a carbene equivalent (NHC-e) were added, and after replacement with nitrogen gas, 1.0 mL (1.0 mmol) of 1 M KO$^t$Bu (solution in THF), 3 mL of toluene, 0.77 mL (5.0 mmol) of aniline, and 0.98 mL (5.0 mmol) of benzyl alcohol were added, and then stirred at 150° C. for 5 hours. After cooling, the reactant was analyzed by GC, and N-benzylaniline was obtained with a GC yield of 49%.

Comparative Example 1

Hydrogenation of Methyl Benzoate Using Ruthenium Complex Described in Patent Document 1

[Chemical Formula 31]

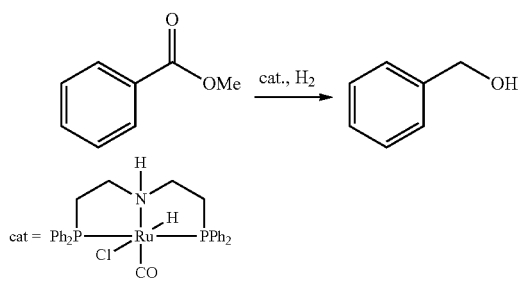

In a 1004 l stainless autoclave, 1.5 mg (0.0025 mmol) of the aforementioned ruthenium complex (hereinafter, referred to as comparative complex A) was added, and after replacement with nitrogen gas, 0.25 mL (0.25 mmol) of 1 MKO$^t$Bu (solution in THF), 2 mL of toluene, and 0.31 mL (2.5 mmol) of a substrate were added, and then stirred at 1 MPa of hydrogen pressure at 80° C. for 6 hours. After cooling, the reactant was analyzed by GC, and benzyl alcohol was obtained with a GC yield of 47%.

Comparative Example 2

Hydrogenation of Methyl Benzoate Using Ruthenium Complex Described in Patent Document 1

In a 100 mL stainless autoclave, 3.6 mg (0.0060 mmol) of comparative complex A, and 1.3 mg (0.0059 mmol) of a carbene equivalent (NHC-d) were added, and after replacement with nitrogen gas, 0.6 mL (0.6 mmol) of 1 M KO$^t$Bu (solution in THF), 4.8 mL of toluene, and 0.72 mL (6.0 mmol) of a substrate were added, and then stirred at 1 MPa of hydrogen pressure at 80° C. for 6 hours. After cooling, the reactant was analyzed by GC, and benzyl alcohol was obtained with a GC yield of 47%.

Comparative Example 3

Hydrogenation of N,N-Dimethylbenzamide Using Ruthenium Complex Described in Patent Document 1

In a 100 mL stainless autoclave, 3.6 mg (0.0060 mmol/Ru) of comparative complex A was added, and after replacement with nitrogen gas, 0.12 mL (0.12 mmol) of 1 MKO$^t$Bu (solution in THF), 1 mL of toluene, and 180 mg (1.2 mmol) of a substrate were added, and then stirred at 3 MPa of hydrogen pressure at 100° C. for 6 hours. After cooling, the reactant was analyzed by GC, and benzyl alcohol was obtained with a GC yield of 43%.

Comparative Example 4

Hydrogenation of Methyl Benzoate Using Ruthenium Complex C

In a 100 mL stainless autoclave, 1.5 mg (0.0024 mmol/Ru) of ruthenium complex C produced in Example 4 was added, and after replacement with nitrogen gas, 0.25 mL (0.25 mmol) of 1 M KO$^t$Bu (solution in THF), 2 mL of toluene, and 0.31 mL (2.5 mmol) of a substrate were added, and then stirred at 1 MPa of hydrogen pressure at 80° C. for 6 hours. After cooling, the reactant was analyzed by GC, and benzyl alcohol was obtained with a GC yield of 7%.

Comparative Example 5

Hydrogenation of Methyl Benzoate Using Ruthenium Complex I

In a 100 mL stainless autoclave, 1.5 mg (0.0025 mmol/Ru) of ruthenium complex I produced in Example 10 was added, and after replacement with nitrogen gas, 0.25 mL (0.25 mmol) of 1 M KO$^t$Bu (solution in THF), 2 mL of toluene, and 0.31 mL (2.5 mmol) of a substrate were added, and then stirred at 1 MPa of hydrogen pressure at 80° C. for 6 hours. After cooling, the reactant was analyzed by GC, and benzyl alcohol was not observed.

INDUSTRIAL APPLICABILITY

The present invention provides a novel ruthenium complex featured by having a bis (phosphinoalkyl)amine as a tridentate ligand, and having an N-heterocyclic carbene as a monodentate ligand. The ruthenium complex of the present invention can be prepared easily from an inorganic ruthenium compound that is low in cost and easily available. The novel ruthenium complex of the present invention catalyzes hydrogenation of ketones, aldehydes, esters and amides in the presence of a hydrogen donor. Also it catalyzes dehydrogenation reaction of alcohols, hemiacetals and hemiaminals, and N-alkylation via condensation between alcohols and amines. The novel ruthenium complex shows high catalytic activity under a relatively gentle reaction condition. In particular, in hydrogenation of esters, reaction under an atmospheric pressure of hydrogen that was difficult in ruthenium complexes reported heretofore is enabled. Also, the ruthenium complex of the present invention is weighable powder in air, and easy to handle, so that it is suited for industrial use. Further, the ruthenium complex of the present invention allows various reaction conditions depending on the situation because the reaction is conducted while a complex is formed. Therefore, the ruthenium complex of the present invention and the reaction using the same are useful in the field of organic industrial chemistry.

The invention claimed is:
1. A ruthenium complex represented by the following general formula (1):

$$RuX^1X^2(PNP)(NHC)_m(Solv)_n \qquad (1)$$

(in the general formula (1), $X^1$ and $X^2$ each independently represent a monovalent anionic monodentate ligand; PNP represents a tridentate ligand represented by the following general formula (2):

(2)

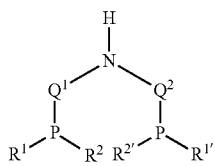

(in the general formula (2), $R^1$, $R^2$, $R^{1'}$ and $R^{2'}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^1$ and $R^2$, and $R^{1'}$ and $R^{2'}$ each independently may bind to each other to form a ring together with the adjacent phosphorus atom; $Q^1$ and $Q^2$ each independently represent an optionally substituted alkanediyl group or an optionally substituted aralkylene group), NHC represents an N-heterocyclic carbene derived from a nitrogen-containing heterocyclic ring, and Solv represents a coordinating solvent; m represents an integer from 1 to 3, n represents an integer from 0 to 2, and $1 \leq m+n \leq 3$).

2. The ruthenium complex according to claim 1, wherein the PNP is a tridentate ligand represented by the following general formula (3):

(3)

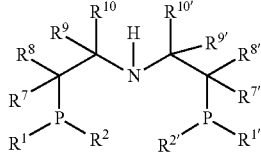

(in the general formula (3), $R^1$, $R^2$, $R^{1'}$ and $R^{2'}$ represent the groups having the same definition as in the general formula (2); $R^7$, $R^{7'}$, $R^8$, $R^{8'}$, $R^9$, $R^{9'}$, $R^{10}$ and $R^{10'}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^7$, and $R^8$ or $R^9$ or $R^{10}$, $R^{7'}$, and $R^{8'}$ or $R^{9'}$ or $R^{10'}$, $R^8$, and $R^9$ or $R^{10}$, $R^{8'}$, and $R^{9'}$ or $R^{10'}$, $R^9$, and $R^{10}$ or $R^{9'}$ or $R^{10'}$, $R^{9'}$, and $R^{10}$ or $R^{10'}$ and $R^{10}$ and $R^{10'}$ each independently may bind to each other to form a ring together with the adjacent carbon atom(s)).

3. The ruthenium complex according to claim 2, wherein the PNP is a tridentate ligand represented by the following general formula (4):

(4)

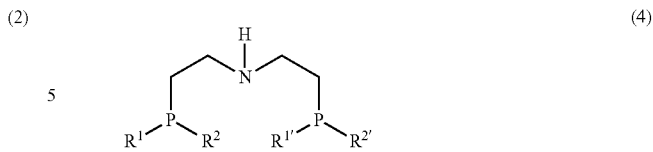

(in the general formula (4), $R^1$, $R^2$, $R^{1'}$ and $R^{2'}$ represent the groups having the same definition as in general formula (2)).

4. The ruthenium complex according to claim 3, wherein $R^1$, $R^2$, $R^{1'}$ and $R^{2'}$ each independently represent an optionally substituted alkyl group, an optionally substituted aryl group or an optionally substituted aralkyl group.

5. The ruthenium complex according to claim 4, wherein NHC is any one of N-heterocyclic carbene selected from the group consisting of imidazole-ylidenes, dihydroimidazole-ylidenes, thiazole-ylidenes, dihydropyrimidine-ylidenes, hexahydro-1,3-diazepine-ylidenes, dihydrothiazole-ylidenes, oxazole-ylidenes, dihydrooxazole-ylidenes, tetrahydropyrimidine-ylidenes, pyrimidine-ylidenes and triazole-ylidenes.

6. The ruthenium complex according to claim 5, wherein the NHC is imidazole-2-ylidenes or dihydroimidazole-2-ylidenes represented by the following general formula (5) or (6):

(5)

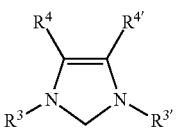

(6)

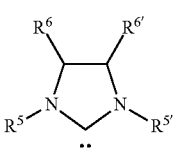

(in the general formulas (5) and (6), $R^3$, $R^{3'}$, $R^5$ and $R^{5'}$ each independently represent an alkyl group, an aryl group, an aralkyl group, an alkenyl group, an alkynyl group or a heterocyclic group, and these alkyl group, aryl group, aralkyl group, alkenyl group, alkynyl group and heterocyclic group may have substituent(s); $R^4$, $R^{4'}$, $R^6$ and $R^{6'}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^3$ and $R^{3'}$, $R^3$ and $R^4$, $R^4$ and $R^{4'}$ and $R^{4'}$ and $R^{3'}$ each independently may bind to each other to form a ring together with the adjacent atoms; $R^5$ and $R^{5'}$, $R^5$ and $R^6$, $R^6$ and $R^{6'}$ and $R^{6'}$ and $R^{5'}$ each independently may bind to each other to form a ring together with the adjacent atoms).

7. The ruthenium complex according to claim 6, wherein $R^3$, $R^{3'}$, $R^5$ and $R^{5'}$ each independently represent an optionally substituted alkyl group or an optionally substituted aryl group, and $R^4$, $R^{4'}$, $R^6$ and $R^{6'}$ each independently represent a hydrogen atom, an optionally substituted alkyl group or an optionally substituted aryl group.

8. The ruthenium complex according to claim 1, wherein the PNP and/or NHC is an optically active form.

9. A method for producing the ruthenium complex represented by the following general formula (1):

(in the general formula (1), $X^1$, $X^2$, PNP, NHC, Solv, m and n are the same as those defined in claim 1), comprising:

a ruthenium complex represented by the following general formula (7):

$$[RuX^1X^2(PNP)]_q \qquad (7)$$

(in the general formula (7), $X^1$ and $X^2$ each independently represent a monovalent anionic monodentate ligand, PNP represents a tridentate ligand represented by the general formula (2), (3) or (4) or an optically active form thereof, and q represents an integer from 1 to 2) is reacted with NHC (NHC represents an N-heterocyclic carbene derived from nitrogen-containing heterocyclic ring or an optically active form thereof) or an NHC equivalent, wherein the general formula (2) is:

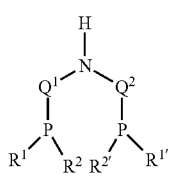

(in the general formula (2), $R^1$, $R^2$, $R^{1\prime}$ and $R^{2\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^1$ and $R^2$, and $R^{1\prime}$ and $R^{2\prime}$ each independently may bind to each other to form a ring together with the adjacent phosphorus atom; $Q^1$ and $Q^2$ each independently represent an optionally substituted alkanediyl group or an optionally substituted aralkylene group), NHC represents an N-heterocyclic carbene derived from a nitrogen-containing heterocyclic ring, and Solv represents a coordinating solvent; m represents an integer from 1 to 3, n represents an integer from 0 to 2, and 1≤m+n≤3)

wherein the general formula (3) is

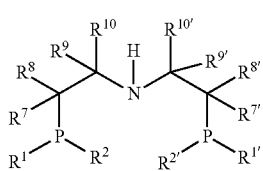

(in the general formula (3), $R^1$, $R^2$, $R^{1\prime}$ and $R^{2\prime}$ represent the groups having the same definition as in the general formula (2); $R^7$, $R^{7\prime}$, $R^8$, $R^{8\prime}$, $R^9$, $R^{9\prime}$, $R^{10}$ and $R^{10\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^7$, and $R^8$ or $R^9$ or $R^{10}$, $R^{7\prime}$, and $R^{8\prime}$ or $R^{9\prime}$ or $R^{10\prime}$, $R^8$, and $R^9$ or $R^{10}$, $R^{8\prime}$, and $R^{9\prime}$ or $R^{10\prime}$, $R^9$, and $R^{10}$ or $R^{9\prime}$ or $R^{10\prime}$, $R^{9\prime}$, and $R^{10}$ or $R^{10\prime}$ and $R^{10}$ and $R^{10\prime}$ each independently may bind to each other to form a ring together with the adjacent carbon atom(s); and wherein the general formula (4) is

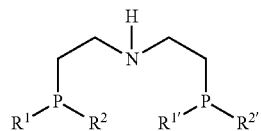

(in the general formula (4), $R^1$, $R^2$, $R^{1\prime}$ and $R^{2\prime}$ represent the groups having the same definition as in general formula (2).

10. A method for producing the ruthenium complex represented by the following general formula (1):

(in the general formula (1), $X^1$, $X^2$, PNP, NHC, Solv, m and n are the same as those defined in claim 1), comprising:

a ruthenium complex represented by the following general formula (8):

(in the general formula (8), $X^1$ and $X^2$ each independently represent a monovalent anionic monodentate ligand, arene represents an aromatic compound, NHC represents an N-heterocyclic carbene derived from a nitrogen-containing heterocyclic ring or an optically active form thereof) is reacted with PNP (PNP represents a tridentate ligand represented by the general formula (2), (3) or (4) or an optically active form thereof), wherein the general formula (2) is:

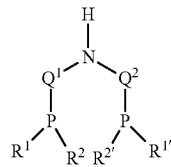

(in the general formula (2), $R^1$, $R^2$, $R^{1\prime}$ and $R^{2\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^1$ and $R^2$, and $R^{1\prime}$ and $R^{2\prime}$ each independently may bind to each other to form a ring together with the adjacent phosphorus atom; $Q^1$ and $Q^2$ each independently represent an optionally substituted alkanediyl group or an optionally substituted aralkylene group), NHC represents an N-heterocyclic carbene derived from a nitrogen-containing heterocyclic ring, and Solv represents a coordinating solvent; m represents an integer from 1 to 3, n represents an integer from 0 to 2, and 1≤m+n≤3)

wherein the general formula (3) is

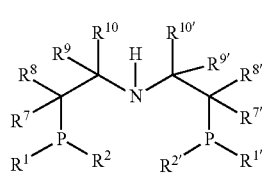

(3)

(in the general formula (3), $R^1$, $R^2$, $R^{1\prime}$ and $R^{2\prime}$ represent the groups having the same definition as in the general formula (2); $R^7$, $R^{7\prime}$, $R^8$, $R^{8\prime}$, $R^9$, $R^{9\prime}$, $R^{10}$ and $R^{10\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^7$, and $R^8$ or $R^9$ or $R^{10}$, $R^{7\prime}$, and $R^{8\prime}$ or $R^{9\prime}$ or $R^{10\prime}$, $R^8$, and $R^9$ or $R^{10}$, $R^{8\prime}$, and $R^{9\prime}$ or $R^{10\prime}$, $R^9$, and $R^{10}$ or $R^{9\prime}$ or $R^{10\prime}$, $R^{9\prime}$, and $R^{10}$ or $R^{10\prime}$ and $R^{10}$ and $R^{10\prime}$ each independently may bind to each other to form a ring together with the adjacent carbon atom(s); and wherein the general formula (4) is

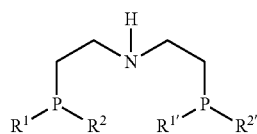

(4)

(in the general formula (4), $R^1$, $R^2$, $R^{1\prime}$ and $R^{2\prime}$ represent the groups having the same definition as in general formula (2).

11. A method for producing alcohol, aldehyde, hemiacetal, hemiaminal, amine, carbonyl compound or N-alkylamine compound, comprising:
using the ruthenium complex according to claim 1 in the reaction system as a catalyst.

12. The method according to claim 11, wherein the alcohol is obtained by hydrogenation of ketone using the ruthenium complex according to claim 1 as a catalyst.

13. The method according to claim 11, wherein the alcohol is obtained by hydrogenation of aldehyde using the ruthenium complex according to claim 1 as a catalyst.

14. The method according to claim 11, wherein the alcohol, the aldehyde or the hemiacetal is obtained by hydrogenation of ester using the ruthenium complex according to claim 1 as a catalyst.

15. The method according to claim 11, wherein the alcohol, the aldehyde, the hemiaminal or the amine is obtained by hydrogenation of amide using the ruthenium complex according to claim 1 a catalyst.

16. The method according to claim 11, wherein the carbonyl compound is obtained by dehydrogenation of alcohol, hemiacetal or hemiaminal using the ruthenium complex according to claim 1 as a catalyst.

17. The method according to claim 11, wherein the N-alkylamine compound is obtained via condensation between alcohol and amine, using the ruthenium complex according to claim 1 as a catalyst.

18. The method according to claim 11, wherein in place of the ruthenium complex according to claim 1, a ruthenium complex represented by the following general formula (7)

$$[RuX^1X^2(PNP)]_q \quad (7)$$

(in the general formula (7), $X^1$ and $X^2$ each independently represent a monovalent anionic monodentate ligand, PNP represents a tridentate ligand represented by the general formula (2), (3) or (4) or an optically active form thereof, and q represents an integer from 1 to 2), and NHC (NHC represents an N-heterocyclic carbene derived from a nitrogen-containing heterocyclic ring, or an optically active form thereof) or an NHC equivalent are respectively added into the reaction system to function as catalyst, wherein the general formula (2) is:

is:

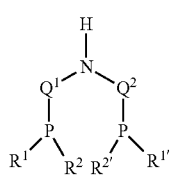

(2)

(in the general formula (2), $R^1$, $R^2$, $R^{1\prime}$ and $R^{2\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^1$ and $R^2$, and $R^{1\prime}$ and $R^{2\prime}$ each independently may bind to each other to form a ring together with the adjacent phosphorus atom; $Q^1$ and $Q^2$ each independently represent an optionally substituted alkanediyl group or an optionally substituted aralkylene group), NHC represents an N-heterocyclic carbene derived from a nitrogen-containing heterocyclic ring, and Solv represents a coordinating solvent; m represents an integer from 1 to 3, n represents an integer from 0 to 2, and 1≤m+n≤3) wherein the general formula (3) is

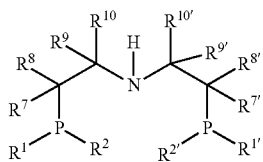

(3)

(in the general formula (3), $R^1$, $R^2$, $R^{1\prime}$ and $R^{2\prime}$ represent the groups having the same definition as in the general formula (2); $R^7$, $R^{7\prime}$, $R^8$, $R^{8\prime}$, $R^9$, $R^{9\prime}$, $R^{10}$ and $R^{10\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^7$, and $R^8$ or $R^9$ or $R^{10}$, $R^{7\prime}$, and $R^{8\prime}$ or $R^{9\prime}$ or $R^{10\prime}$, $R^8$, and $R^9$ or $R^{10}$, $R^{8\prime}$, and $R^{9\prime}$ or $R^{10\prime}$, $R^9$, and $R^{10}$ or $R^{9\prime}$ or $R^{10\prime}$, $R^{9\prime}$, and $R^{10}$ or $R^{10\prime}$ and $R^{10}$ and $R^{10\prime}$ each independently may bind to each other to form a ring together with the adjacent carbon atom(s); and wherein the general formula (4) is

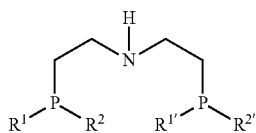

(4)

(in the general formula (4), $R^1$, $R^2$, $R^{1\prime}$ and $R^{2\prime}$ represent the groups having the same definition as in general formula (2).

19. The method according to claim 11, wherein in place of the ruthenium complex according to claim 1, a ruthenium complex represented by the following general formula (8):

$$RuX^1X^2(arene)(NHC) \qquad (8)$$

(in the general formula (8), $X^1$ and $X^2$ each independently represent a monovalent anionic monodentate ligand, arene represents an aromatic compound, NHC represents an N-heterocyclic carbene derived from a nitrogen-containing heterocyclic ring or an optically active form thereof), and PNP (PNP represents a tridentate ligand represented by the general formula (2), (3) or (4) or an optically active form thereof) are respectively added into the reaction system to function as catalyst, wherein the general formula (2) is:

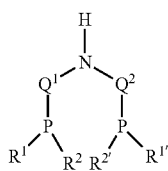

(2)

(in the general formula (2), $R^1$, $R^2$, $R^{1\prime}$ and $R^{2\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^1$ and $R^2$, and $R^{1\prime}$ and $R^{2\prime}$ each independently may bind to each other to form a ring together with the adjacent phosphorus atom; $Q^1$ and $Q^2$ each independently represent an optionally substituted alkanediyl group or an optionally substituted aralkylene group), NHC represents an N-heterocyclic carbene derived from a nitrogen-containing heterocyclic ring, and Solv represents a coordinating solvent; m represents an integer from 1 to 3, n represents an integer from 0 to 2, and $1 \le m+n \le 3$)

wherein the general formula (3) is

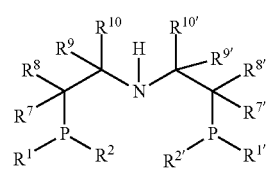

(3)

(in the general formula (3), $R^1$, $R^2$, $R^{1\prime}$ and $R^{2\prime}$ represent the groups having the same definition as in the general formula (2); $R^7$, $R^{7\prime}$, $R^8$, $R^{8\prime}$, $R^9$, $R^{9\prime}$, $R^{10}$ and $R^{10\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among these groups, an alkyl group, an aryl group, an aralkyl group, an alkenyl group, an alkynyl group, an alkoxy group, an aryloxy group, an aralkyloxy group and a heterocyclic group may have substituent(s); $R^7$, and $R^8$ or $R^9$ or $R^{10}$, $R^{7\prime}$, and $R^{8\prime}$ or $R^{9\prime}$ or $R^{10\prime}$, $R^8$, and $R^9$ or $R^{10}$, $R^{8\prime}$, and $R^{9\prime}$ or $R^{10\prime}$, $R^9$, and $R^{10}$ or $R^{9\prime}$ or $R^{10\prime}$, $R^{9\prime}$, and $R^{10}$ or $R^{10\prime}$ and $R^{10}$ and $R^{10\prime}$ each independently may bind to each other to form a ring together with the adjacent carbon atom(s); and wherein the general formula (4) is

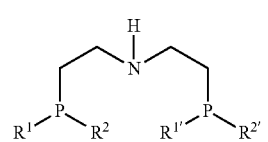

(4)

(in the general formula (4), $R^1$, $R^2$, $R^{1\prime}$ and $R^{2\prime}$ represent the groups having the same definition as in general formula (2).

* * * * *